United States Patent
Stegemann et al.

(10) Patent No.: US 10,668,291 B2
(45) Date of Patent: Jun. 2, 2020

(54) IMPINGEMENT DETECTION FOR IMPLANTABLE MEDICAL DEVICES

(71) Applicant: Medtronic, Inc., Minneapolis, MN (US)

(72) Inventors: Berthold Stegemann, Kassel (DE); Richard Cornelussen, Maastricht (NL); Robert W. Stadler, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 238 days.

(21) Appl. No.: 15/969,387

(22) Filed: May 2, 2018

(65) Prior Publication Data
US 2019/0275337 A1      Sep. 12, 2019

Related U.S. Application Data

(60) Provisional application No. 62/639,376, filed on Mar. 6, 2018.

(51) Int. Cl.
| | |
|---|---|
| *A61N 1/365* | (2006.01) |
| *A61B 5/0245* | (2006.01) |
| *A61B 5/11* | (2006.01) |
| *A61B 5/00* | (2006.01) |
| *A61B 5/06* | (2006.01) |

(Continued)

(52) U.S. Cl.
CPC ........ *A61N 1/36578* (2013.01); *A61B 5/0245* (2013.01); *A61B 5/067* (2013.01); *A61B 5/1102* (2013.01); *A61B 5/6869* (2013.01); *A61B 5/6885* (2013.01); *A61N 1/025* (2013.01); *A61N 1/057* (2013.01); *A61N 1/37205* (2013.01);

(Continued)

(58) Field of Classification Search
CPC .... A61N 1/025; A61N 1/057; A61N 1/36578; A61N 1/37205; A61N 1/37211; A61N 1/3956; A61B 5/0245; A61B 5/067; A61B 5/1102; A61B 5/6869
See application file for complete search history.

(56) References Cited

U.S. PATENT DOCUMENTS

| | | |
|---|---|---|
| 4,955,376 A | 9/1990 | Callaghan et al. |
| 5,117,824 A | 6/1992 | Keimel et al. |

(Continued)

FOREIGN PATENT DOCUMENTS

EP      2271403 B1    12/2011

OTHER PUBLICATIONS

U.S. Appl. No. 15/928,773, filed by Robert W. Stadler, et al., filed Mar. 22, 2018.

(Continued)

*Primary Examiner* — Christopher A Flory

(57) ABSTRACT

In some examples, a system may be used for delivering cardiac therapy or cardiac sensing. The system may include an in implantable medical device including a housing configured to be implanted on or within a heart of a patient, a fixation element configured to attach the housing to the heart; and a sensor configured to produce a signal that indicates motion of the implantable medical device. Processing circuitry may be configured to identify one or more impingements between the housing and another structure, such as a tissue of the heart, based on the signal from the sensor and provide an indication of the one or more impingements to a user.

31 Claims, 18 Drawing Sheets

(51) Int. Cl.
*A61N 1/02* (2006.01)
*A61N 1/372* (2006.01)
*A61N 1/39* (2006.01)
*A61N 1/05* (2006.01)

(52) U.S. Cl.
CPC ........ *A61N 1/37211* (2013.01); *A61N 1/3956* (2013.01); *A61B 2562/0219* (2013.01)

(56) References Cited

U.S. PATENT DOCUMENTS

| | | | |
|---|---|---|---|
| 5,833,603 A * | 11/1998 | Kovacs | A61B 1/00016 600/317 |
| 6,393,316 B1 | 5/2002 | Gillberg et al. | |
| 6,704,598 B2 | 3/2004 | Ding et al. | |
| 6,871,086 B2 | 3/2005 | Nevo et al. | |
| 6,871,096 B2 | 3/2005 | Hill | |
| 7,139,610 B2 | 11/2006 | Ferek-Petric | |
| 7,181,286 B2 | 2/2007 | Burnes et al. | |
| 7,684,863 B2 | 3/2010 | Parikh et al. | |
| 8,145,308 B2 | 3/2012 | Sambelashvili et al. | |
| 8,521,268 B2 | 8/2013 | Zhang et al. | |
| 8,521,284 B2 | 8/2013 | Kim et al. | |
| 8,649,866 B2 | 2/2014 | Brooke | |
| 8,750,998 B1 | 6/2014 | Ghosh et al. | |
| 9,403,019 B2 | 8/2016 | Sambelashvili et al. | |
| 9,717,923 B2 | 8/2017 | Thompson-nauman et al. | |
| 9,789,319 B2 | 10/2017 | Sambelashvili et al. | |
| 10,307,604 B2 * | 6/2019 | Hastings | A61N 1/0573 |
| 2004/0167416 A1 | 8/2004 | Lee | |
| 2004/0171924 A1 * | 9/2004 | Mire | A61B 34/20 600/407 |
| 2005/0209649 A1 * | 9/2005 | Ferek-petric | A61N 1/36514 607/17 |
| 2006/0094951 A1 * | 5/2006 | Dean | A61F 2/30942 600/407 |
| 2006/0149143 A1 * | 7/2006 | Colvin, Jr. | G01N 21/552 600/316 |
| 2006/0155338 A1 | 7/2006 | Mongeon et al. | |
| 2007/0250127 A1 | 10/2007 | Stylos et al. | |
| 2007/0293895 A1 * | 12/2007 | Cowan | A61N 1/3787 607/5 |
| 2009/0149911 A1 * | 6/2009 | Dacey, Jr. | A61N 1/36014 607/45 |
| 2009/0204168 A1 * | 8/2009 | Kallmyer | A61N 1/372 607/27 |
| 2009/0204170 A1 * | 8/2009 | Hastings | A61N 1/37205 607/33 |
| 2009/0259216 A1 * | 10/2009 | Drew | A61N 1/3706 604/891.1 |
| 2009/0276001 A1 | 11/2009 | Busacker et al. | |
| 2009/0281590 A1 * | 11/2009 | Maskara | A61N 1/3627 607/25 |
| 2010/0137935 A1 | 6/2010 | Parikh et al. | |
| 2010/0198291 A1 | 8/2010 | Sambelashvili et al. | |
| 2011/0071411 A1 | 3/2011 | Shuros et al. | |
| 2012/0090627 A1 | 4/2012 | Ransbury et al. | |
| 2012/0109236 A1 | 5/2012 | Jacobson et al. | |
| 2013/0053906 A1 | 2/2013 | Ghosh et al. | |
| 2014/0081354 A1 * | 3/2014 | Davis | A61N 1/372 607/59 |
| 2014/0236172 A1 * | 8/2014 | Hastings | A61N 1/057 606/129 |
| 2014/0276928 A1 | 9/2014 | Vanderpool et al. | |
| 2014/0277245 A1 | 9/2014 | Lu et al. | |
| 2014/0330248 A1 | 11/2014 | Thompson-nauman et al. | |
| 2014/0330287 A1 | 11/2014 | Thompson-nauman et al. | |
| 2015/0142069 A1 | 5/2015 | Sambelashvili | |
| 2016/0175603 A1 | 6/2016 | Sheldon et al. | |
| 2016/0310031 A1 | 10/2016 | Sarkar | |
| 2017/0056649 A1 | 3/2017 | Kane et al. | |

OTHER PUBLICATIONS

U.S. Appl. No. 15/928,714, filed by Robert W. Stadler et al., filed Mar. 22, 2018.

Szulik, et al., "Assessment of apical rocking: a new, integrative approach for selection of candidates for cardiac resynchronization therapy," European Journal of Echocardiography, 2010, accessed on Dec. 20, 2017, pp. 863-869.

Mada, MD, "New Automatic Tools to Identify Responders to Cardiac Resynchronization Therapy," Journal of the American Society of Echocardiography, vol. 29, No. 10, Oct. 2016, pp. 966-972.

Stankovic, et al., "Relationship of visually assessed apical rocking and septal flash to response and long-term survival following cardiac resynchronization therapy (PREDICT-CRT)," European Heart Journal, Cardiovascular Imaging, 2016, accessed on Dec. 20, 2017, pp. 262-269.

(PCT/2019/020534) PCT Notification of Transmittal of the International Search Report and the Written Opinion of the International Searching Authority, dated Jun. 3, 2019, 12 pages.

\* cited by examiner

FIG. 12A
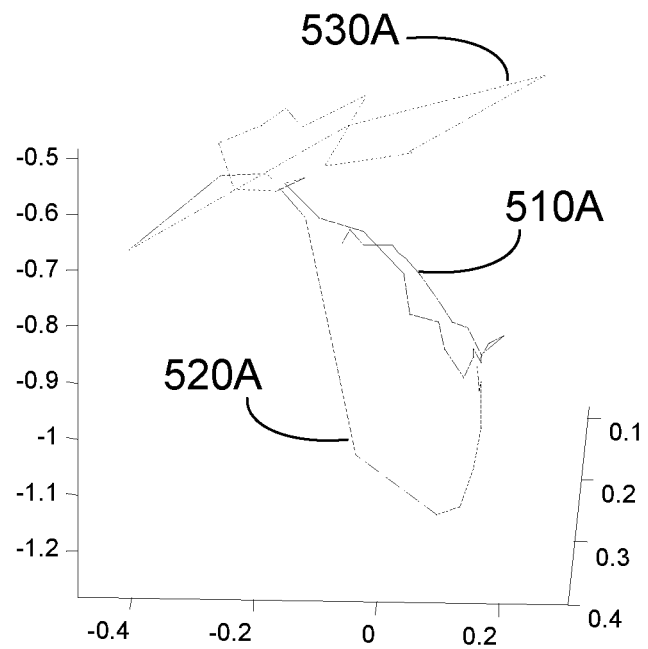
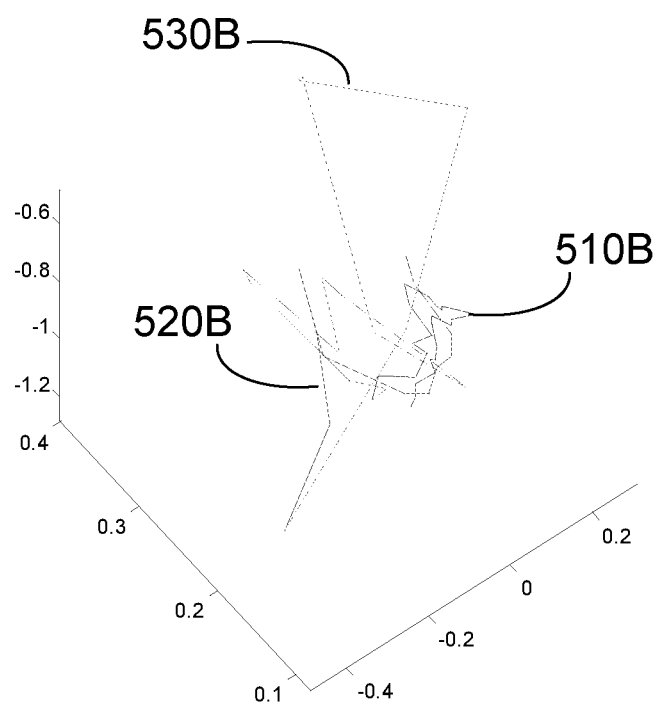
FIG. 12B

FIG. 13A
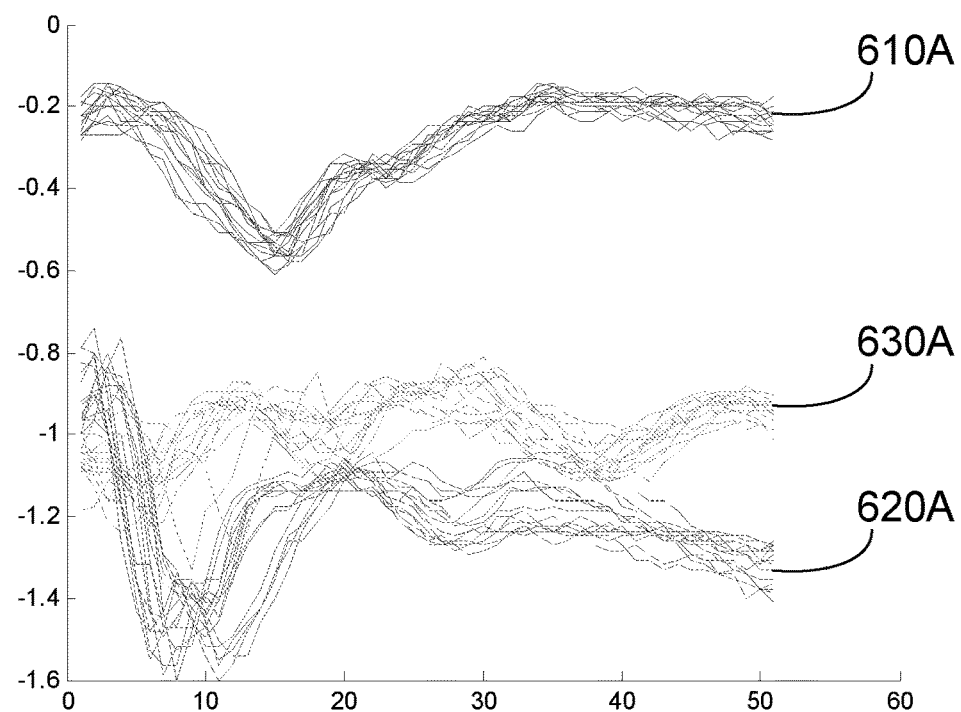
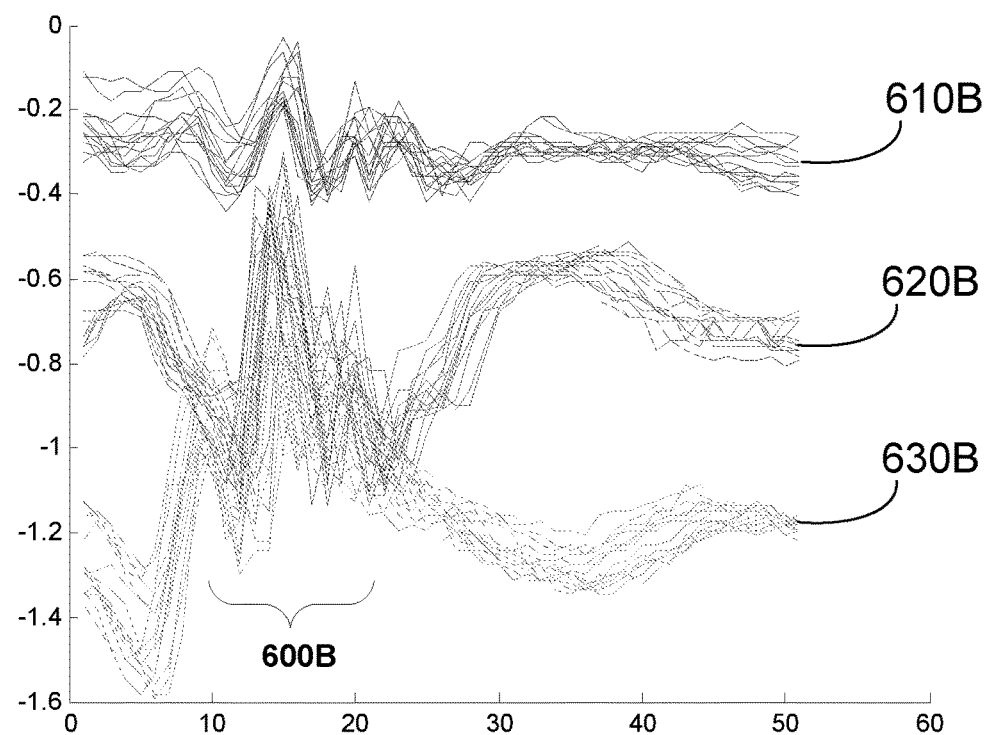
FIG. 13B

FIG. 13C
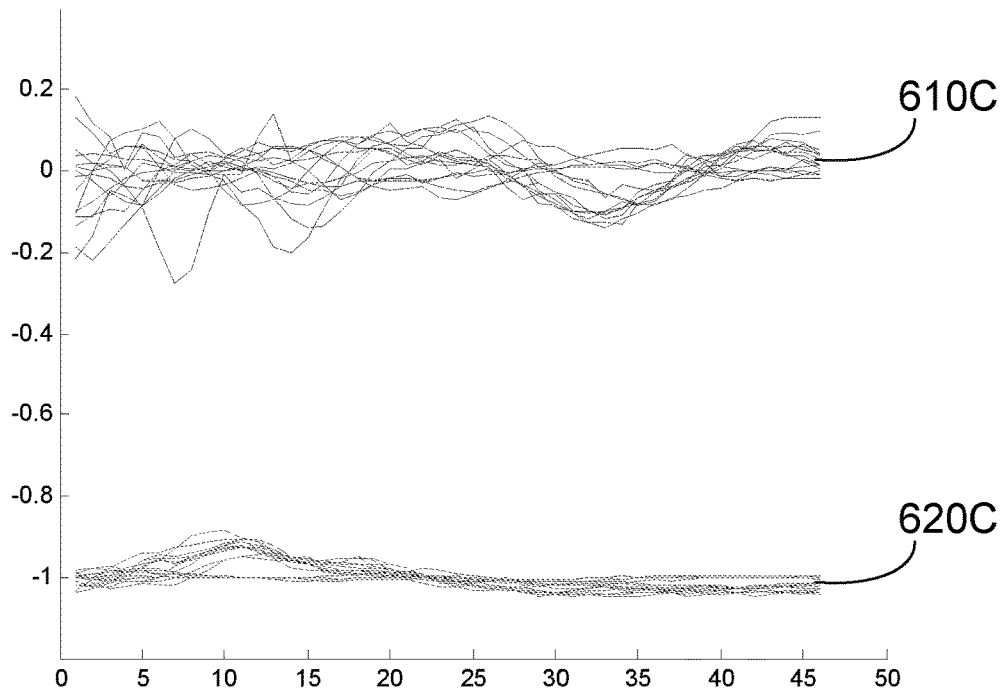
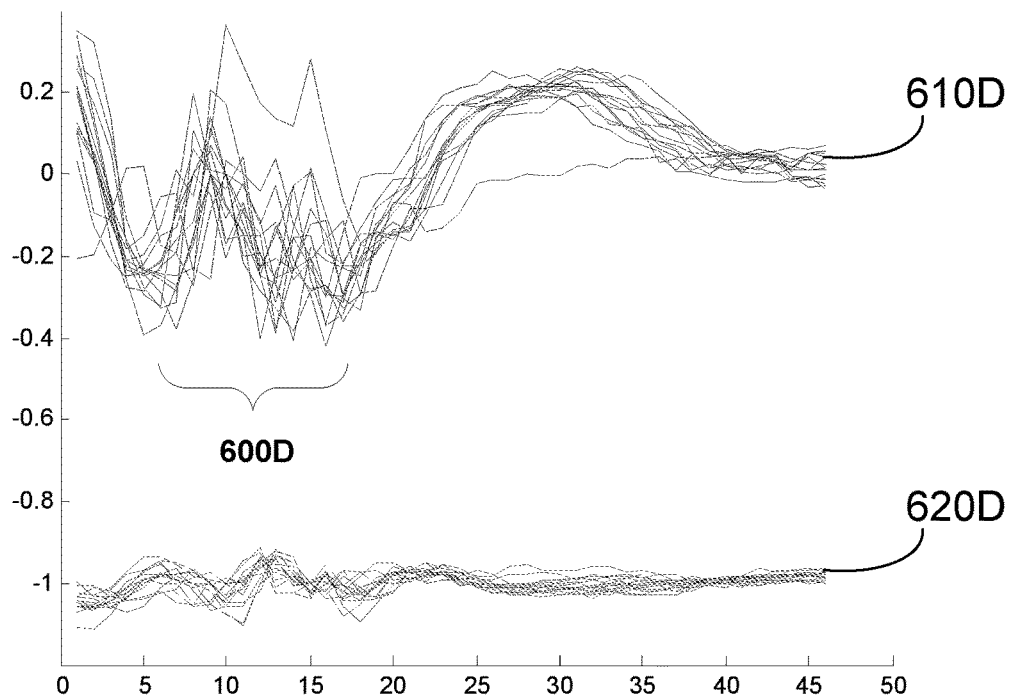
FIG. 13D

IMPINGEMENT DETECTION FOR IMPLANTABLE MEDICAL DEVICES

This application claims the benefit of U.S. Provisional Patent Application Ser. No. 62/639,376, entitled, "IMPINGEMENT DETECTION FOR IMPLANTABLE MEDICAL DEVICES," and filed on Mar. 6, 2018, the entire content of which is incorporated by reference.

TECHNICAL FIELD

The disclosure relates to medical devices, and more particularly medical devices that are configured for implantation on or within the heart.

BACKGROUND

Some types of implantable medical devices, such as cardiac pacemakers or implantable cardioverter defibrillators, monitor physiological conditions and provide therapeutic electrical signals to a heart of a patient, such as bradycardia pacing, cardiac resynchronization therapy (CRT), anti-tachycardia pacing (ATP), and cardioversion/defibrillation shocks. Medical device technology advancement has led toward smaller and smaller implantable devices. Recently, cardiac pacemakers have been introduced which may be implanted directly in a heart chamber. In some examples, such pacemakers may be leadless and delivered into the heart chamber using a catheter. Such miniaturized pacemakers may be referred to as intracardiac pacing devices (PDs), although they may be epicardially or extracardially implanted in some examples. An intracardiac PD may be configured to deliver CRT, e.g., as part of a system with one or more other devices.

SUMMARY

Depending upon the location where it is implanted, an intracardiac PD may impinge on, e.g., collide or otherwise mechanically interact with, cardiac structures, such as papillary muscles, cordae, valve structures, or ventricular endocardium, or other non-cardiac structures, such as other implantable medical devices (IMDs), a component of another IMD, or some other non-anatomical structure. In some cases, collisions can result in mechanical damage to the PD or cardiac structures, scar tissue formation, or formation of inflammatory vegetations that can embolize or impede blood flow. In some cases, collisions may impede the performance of one or more sensors of the PD, such as by distorting an accelerometer or other motion sensor signal, which can be used by the PD to track cardiac contractility, patient activity, or the effectiveness of pacing in capturing the heart, as examples. The artifact caused by the impingement may interfere with these uses of the accelerometer. In general, this disclosure is directed to techniques detecting impingement of an IMD, e.g., a PD, with cardiac tissue or other structures. Impingement detection is generally described as occurring during implantation of the IMD but may occur at any time after implantation.

More particularly, the techniques include detecting impingements based on a signal from a sensor that indicates motion of the IMD. The sensor may be a multi-axis accelerometer located within a housing of the IMD. The signal may vary with the mechanical cardiac cycle, and processing circuitry may identify impingements based on characteristics of the signal during a cardiac cycle, such as a frequency exceeding a threshold and/or a magnitude of motion orthogonal to a primary axis of systolic motion exceeding a threshold. By acquiring and analyzing sensor signals, the processing circuitry may determine whether impingement is occurring between the device and other structures during the cardiac cycle. If impingement is occurring, the processing circuitry may inform a user, such as the IMD implanter or other medical professional, of the impingement(s) or impingement severity, which may, for example, encourage the user to seek a different implant site based on an evaluation of the impingement.

In one example, a system for at least one of delivering cardiac therapy or cardiac sensing comprises an implantable medical device including a housing configured for implantation at least one of on or within a heart of a patient, at least one fixation element configured to attach the housing to the heart, and a sensor configured to produce a signal that indicates motion of the implantable medical device. The system further comprises processing circuitry configured to identify one or more impingements between the housing and another structure based on the signal from the sensor and provide an indication of the one or more impingements to a user.

Another example is a method for evaluating implantation of an implantable medical device configured for at least one of delivering cardiac therapy or cardiac sensing. The method comprises producing, by a sensor, a signal that is indicative of a motion of the implantable medical device and identifying one or more impingements between a housing of the implantable medical device and another structure based on the signal from the sensor.

Other examples include a system for evaluating implantation of an implantable medical device configured for at least one of delivering cardiac therapy or cardiac sensing, wherein the implantable medical device is attached by a fixation element to a heart of a patient, the system comprising means for producing, by a sensor, a signal that is indicative of a motion of the implantable medical device and means for identifying one or more impingements between a housing of the implantable medical device and another structure based on the signal from the sensor.

Other examples include a computer-readable storage medium comprising instructions that, when executed by processing circuitry of a medical device system for evaluating implantation of an implantable medical device configured for at least one of delivering cardiac therapy or cardiac sensing, wherein the implantable medical device is attached by a fixation element to a heart of a patient, cause the processing circuitry to produce, by a sensor, a signal that is indicative of a motion of the implantable medical device and identify one or more impingements between a housing of the implantable medical device and another structure based on the signal from the sensor.

Other examples include a system for at least one of delivering cardiac therapy or cardiac sensing comprises an implantable medical device including a housing configured for implantation at least one of on or within a heart of a patient, at least one fixation element configured to attach the housing to the heart, a sensor configured to produce a signal that indicates motion of the implantable medical device, a plurality of electrodes, and signal generation circuitry within the housing, the signal generation circuitry configured to deliver cardiac pacing via the plurality of electrodes. The system further comprises processing circuitry configured to identify a heartbeat, identify one or more impingements between the housing and another structure based on the signal from the sensor, identify one of the impingements during the heartbeat, and provide an indication of the one or more impingements to a user, wherein the processing circuitry comprises processing circuitry of the implantable medical device within the housing configured to control the delivery of pacing by the signal generation circuitry, and wherein the housing is configured for implantation within the left ventricle of the heart.

This summary is intended to provide an overview of the subject matter described in this disclosure. It is not intended to provide an exclusive or exhaustive explanation of the methods and systems described in detail within the accompanying drawings and description below. The details of one or more aspects of the disclosure are set forth in the accompanying drawings and the description below.

BRIEF DESCRIPTION OF DRAWINGS

The details of one or more examples of this disclosure are set forth in the accompanying drawings and the description below. Other features, objects, and advantages of this disclosure will be apparent from the description and drawings, and from the claims.

FIG. 12A is a plot illustrating motion of an IMD during cardiac contraction, in accordance with one or more aspects of this disclosure.

FIG. 12B is a plot illustrating the motion of the IMD with the axes transformed such that the primary axis of motion during systole is out of the plane of the plot and the motion orthogonal to the primary axis is emphasized, in accordance with one or more aspects of this disclosure.

FIGS. 13A and 13B are plots of motion sensor data illustrating motion of the IMD, including the frequency of the motion during systole, in accordance with one or more aspects of this disclosure.

FIGS. 13C and 13D are plots of motion sensor data with axes transformed illustrating motion of the IMD orthogonal to the primary systolic axis during cardiac contraction, in accordance with one or more aspects of this disclosure.

DETAILED DESCRIPTION

As described above, in general, this disclosure describes example techniques related to detecting impingement of an IMD at the time of implant or any time thereafter, e.g., using an IMD such as an intracardiac PD. The introduction of such PDs, and the resulting elimination of the need for transvenous intracardiac leads, provides several advantages. For example, complications due to infection associated with a lead extending from a subcutaneous pacemaker pocket transvenously into the heart may be eliminated. Other complications, such as "twiddler's syndrome," lead fracture, or poor connection of the lead to the pacemaker are eliminated in the use of an intracardiac PD.

On the other hand, the location of the PD within the heart may impinge on cardiac structures. With each beat of the heart, the intracardiac PD may collide with structures such as papillary muscles, cordae, valve structures, or ventricular endocardium. The intracardiac PD may additionally or alternatively collide with other structures, which may or may not be anatomical. Such structures may include another PD or other IMD, or component thereof, such as a fixation tine or other fixation element of another PD, or a lead coupled to another IMD. In some examples, one or more fixation elements of the PD may be broken, and the PD may impinge with a separated portion of a broken fixation element.

As described in greater detail herein, an IMD, such as a PD, or one or more other components of a medical device system including the IMD, may detect whether the IMD is impinging with another structure. In some examples, the detection of impingements may take place during implant of an IMD. In some examples, the detection of impingements may additionally or alternatively occur after implant including, for example, periodically, such as once a minute, once an hour, or once every 24 hours, although other frequencies may also be used.

Figure 1A:
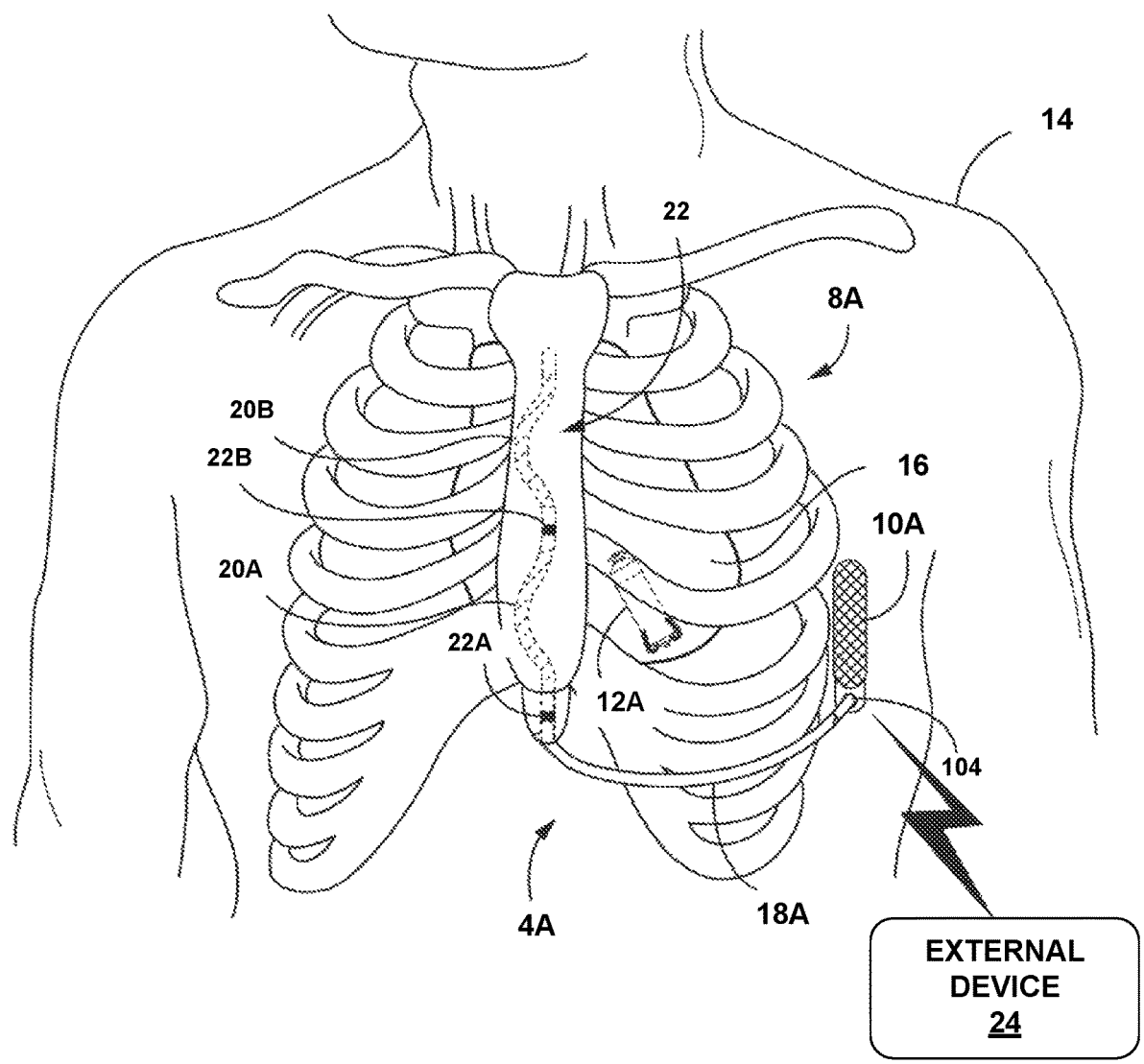
FIG. 1A is a conceptual diagram illustrating an example front view of a patient implanted with an example medical device system that includes an extracardiovascular ICD (EV-ICD) system and a pacing device (PD) that is implanted within a cardiac chamber of the patient in accordance with one or more aspects of this disclosure.
Figure 1B:
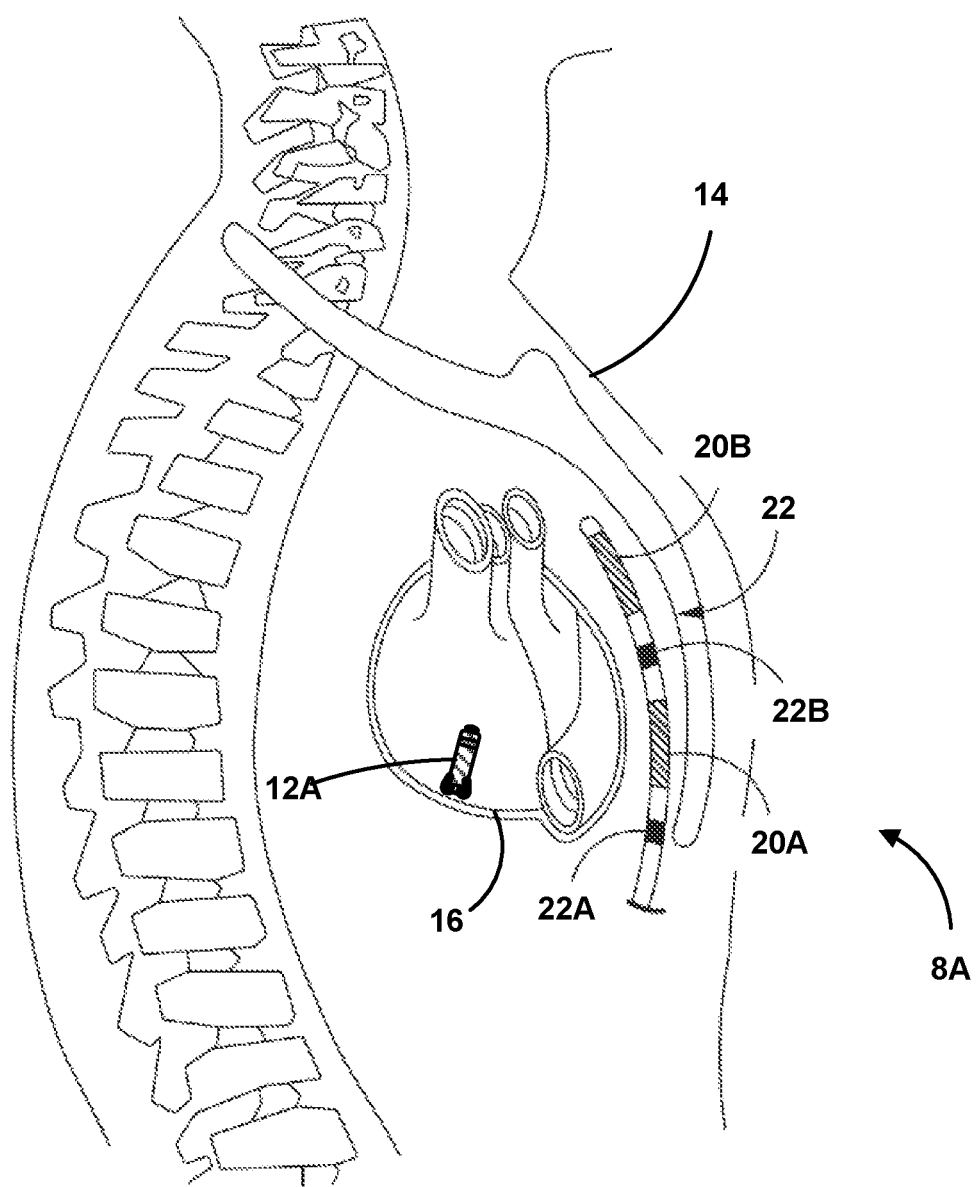
FIG. 1B is a conceptual diagram illustrating an example side view of a patient implanted with the example medical device system of FIG. 1A, in accordance with one or more aspects of this disclosure.
Figure 1C:
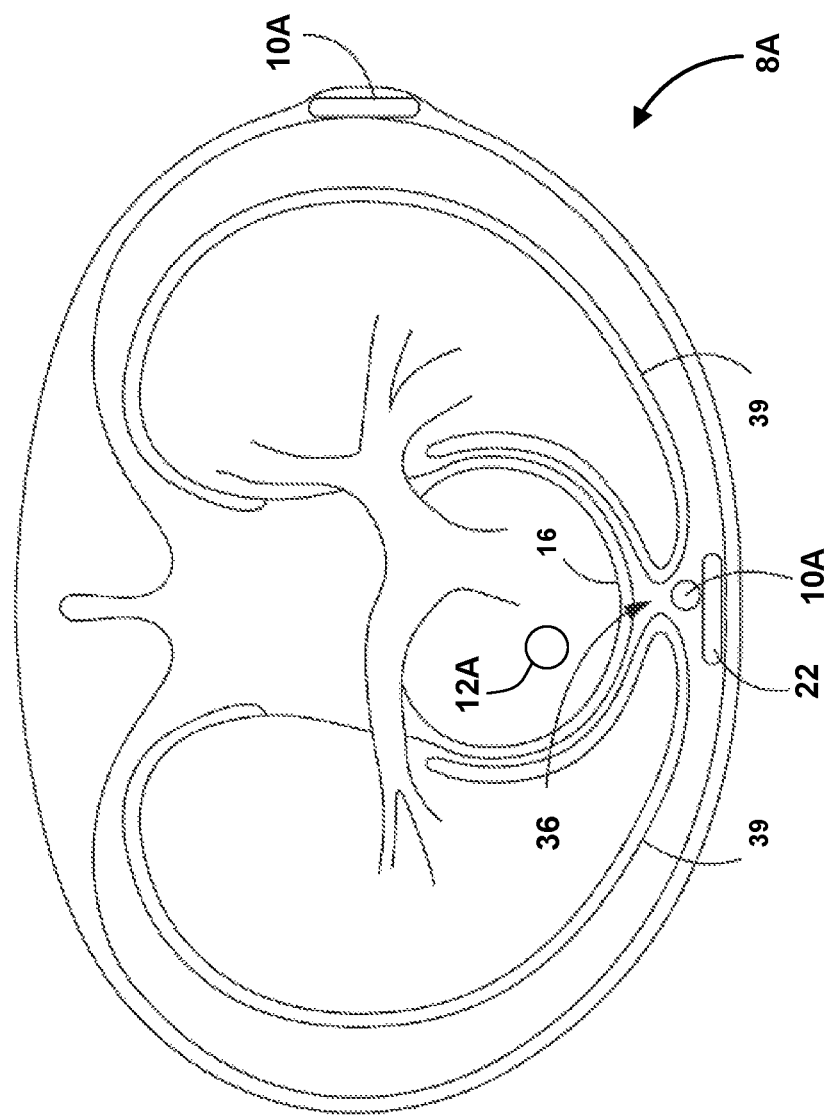
FIG. 1C is a conceptual diagram illustrating an example transverse view of a patient implanted with the example medical device system of FIG. 1A, in accordance with one or more aspects of this disclosure.

FIGS. 1A-1C are conceptual diagrams illustrating various views of an example cardiac medical device system 8A implanted within a patient 14. Components with like numbers in FIGS. 1A-1C may be similarly configured and may provide similar functionality. Medical device system 8A as illustrated in FIGS. 1A-1C may be configured to perform one or more of the techniques described herein with respect to detecting impingement of an IMD, such as a PD, with another structure, such as cardiac tissue.

FIG. 1A is a conceptual diagram illustrating an example front view of a patient implanted with an example cardiac medical device system 8A that includes an extracardiovascular implantable cardioverter defibrillator (ICD) system 4A, and a pacing device (PD) 12A that is implanted within a cardiac chamber of patient 14 in accordance with one or more aspects of this disclosure. PD 12A may be, for example, an implantable leadless pacing device (e.g., a pacemaker) that provides electrical signals to heart 16A via electrodes carried on the housing of PD 12A.

With respect to FIGS. 1A-1C, and elsewhere herein, PD 12A is generally described as being attached within a chamber of heart 16A. That is, PD 12A is described in various portions of this disclosure as an intracardiac pacing device. In other examples that are consistent with aspects of this disclosure, PD 12A may be attached to an external surface of heart 16A, such that PD 12A is disposed outside of heart 16A but may pace a desired chamber. In one example, PD 12A is attached to an external surface of heart 16A, and one or more components of PD 12A may be in contact with the epicardium of heart 16A. Although PD 12A is generally described as a pacing device for intracardiac implantation, PD 12A may alternatively be configured to attach to an external surface of heart 16A and operate as an extracardiac pacing device.

In one example, PD 12A may be implanted within the left or right ventricle of a heart to sense electrical activity of a heart, detect impingement, and/or deliver electrical stimulation to a heart. PD 12A is schematically shown in FIG. 1A attached to a wall of the left ventricle via one or more fixation elements (e.g., tines, helix, etc.) that penetrate the tissue. These fixation elements may secure PD 12A to the cardiac tissue and retain an electrode (e.g., a cathode or an anode) in contact with the cardiac tissue. PD 12A (and PD 12B in FIG. 2) may be implanted at or proximate to the apex of the heart. In other examples, a PD may be implanted at other left-ventricular locations, e.g., on the free-wall or septum.

PD 12A may also include one or more motion sensors (e.g., accelerometers, gyroscopes, or electrical or magnetic field sensors). As will be described in greater detail below, processing circuitry of system 8A, e.g., of PD 12A, may be configured to detect and/or confirm impingement of PD 12A by cardiac tissue or another structure from the motion of PD 12A as indicated by the signal generated by the one or more motion sensors. Collisions between cardiac tissue and PD 12A are examples of impingements. Features of the motion signal that may indicate impingement include, as examples, the presence of a frequency in the signal that is higher than those typically associated with cardiac contraction, and instead indicates collision or other impingement, a velocity of the motion greater than that typically associated with cardiac contraction, or a greater than expected amount of motion occurring in a direction other than the primary direction of motion during a cardiac contraction. In some examples, the features of the motion signal that indicate impingement may vary depending on the posture of the patient, which can be derived from the one or more motion sensors. Consequently, processing circuitry may adjust the motion signal, or thresholds or other criteria applied to the motion signal, based on the posture of the patient to compensate for the posture-based variation of the features and allow effective detection of impingement in a variety of postures.

In examples in which PD 12A is implanted at or near the apex of heart 16, the motion sensor may be correspondingly located at or near the apex. Since PD 12A includes two or more electrodes carried on the exterior housing of PD 12A, no other leads or structures need to reside in other chambers of heart 16. However, in other examples, medical device system 8A may include additional PDs within respective chambers of heart 16 (e.g., left atrium, right atrium), or coupled by leads to electrodes in such chambers of heart.

ICD system 4A includes ICD 10A that is connected to at least one implantable cardiac defibrillation lead 18A (hereinafter, "defibrillation lead 18A"). ICD 10A is configured to deliver high-energy cardioversion or defibrillation shocks to heart 16A of patient 14 in response to atrial fibrillation or ventricular fibrillation being detected. Cardioversion shocks are typically delivered in synchrony with a detected R-wave, when fibrillation detection criteria are met. Defibrillation shocks are typically delivered when fibrillation criteria are met, and the R-wave cannot be discerned from signals sensed by ICD 10A.

ICD 10A of FIG. 1A may be implanted subcutaneously or submuscularly on the left side of patient 14 above the ribcage. FIG. 1C is a conceptual diagram illustrating an example transverse view of a patient implanted with the example medical device system of FIG. 1A, in accordance with one or more aspects of this disclosure. Defibrillation lead 18A of FIG. 1A may be implanted at least partially in a substernal location in FIG. 1A, e.g., between the ribcage and/or sternum 22 and heart. In one such configuration, a proximal portion of defibrillation lead 18A extends subcutaneously from ICD 10A toward the sternum, and a distal portion of lead 18A extends under or below the sternum 22 in the anterior mediastinum 36 (see FIG. 1C). The anterior mediastinum 36 is bounded laterally by the pleurae 39 (see FIG. 1C), posteriorly by the pericardium, and anteriorly by the sternum 22. In some instances, the anterior wall of the anterior mediastinum 36 may also be formed by the transversus thoracis and one or more costal cartilages. The anterior mediastinum 36 includes a quantity of loose connective tissue (such as areolar tissue), some lymph vessels, lymph glands, substernal musculature (e.g., transverse thoracic muscle), branches of the internal thoracic artery, and the internal thoracic vein. In one example, the distal portion of defibrillation lead 18A extends along the posterior side of the sternum 22 substantially within the loose connective tissue and/or substernal musculature of anterior mediastinum 36. Defibrillation lead 18A may be at least partially implanted in other intrathoracic locations, e.g., other non-vascular, extra-pericardial locations, including the gap, tissue, or other anatomical features around the perimeter of and adjacent to, but not attached to, the pericardium or other portion of heart 16A and not above the sternum 22 or ribcage.

In other examples, defibrillation lead 18A may be implanted at other extracardiovascular locations. For example, defibrillation lead 18A may extend subcutaneously above the ribcage from ICD 10A toward a center of the torso of patient 14, bend or turn near the center of the torso, and extend subcutaneously superior above the ribcage and/or sternum 22, like that shown in FIG. 1A. Defibrillation lead 18A may be offset laterally to the left or the right of the sternum 22 or located over the sternum 22. Defibrillation lead 18A may extend substantially parallel to the sternum 22 or be angled lateral from the sternum 22 at either the proximal or distal end. In another example, defibrillation lead 18A and/or a pacing lead or sensing lead may be implanted within the pericardial sac of heart 16A, within the pericardium of heart 16A, epicardially with respect to heart 16A, or at another location.

Defibrillation lead 18A of FIG. 1A may include an insulative lead body having a proximal end that includes a connector configured to be connected to ICD 10A and a distal portion that includes one or more electrodes. Defibrillation lead 18A may also include one or more conductors that form an electrically conductive path within the lead body and interconnect the electrical connector and respective ones of the electrodes.

Defibrillation lead 18A of FIG. 1A includes a defibrillation electrode that, in the illustrated example, includes two sections or segments 20A and 20B. Segments 20A and 20B are collectively (or alternatively) referred to herein as "defibrillation electrodes 20." Defibrillation electrodes 20 of FIG. 1A are positioned toward the distal portion of defibrillation lead 18A, e.g., toward the portion of defibrillation lead 18A extending along sternum 22 of patient 14. Defibrillation lead 18A of FIG. 1A is placed below and/or along sternum 22 such that a therapy vector between defibrillation electrodes 20A or 20B and a housing electrode formed by ICD 10A or on ICD 10A (or other second electrode of the therapy vector) is substantially across a ventricle of heart 16A. The therapy vector may, in one example, be viewed as a line that extends from a point on defibrillation electrodes 20 (e.g., a center of one of the defibrillation electrode sections 20A or 20B) to a point on the housing electrode of ICD 10A. Each of defibrillation electrodes 20 of FIG. 1A may, in one example, be an elongated coil electrode. In some examples, a defibrillation lead may include more or fewer than the two defibrillation electrodes 20 in the illustrated example of defibrillation lead 18A, such as a single coil defibrillation electrode 20.

FIG. 1B is a conceptual diagram illustrating an example side view of a patient implanted with the example medical device system of FIG. 1A, in accordance with one or more aspects of this disclosure. Defibrillation lead 18A may also include one or more sensing electrodes, such as sensing electrodes 22A and 22B, located along the distal portion of defibrillation lead 18A. In the example illustrated in FIGS. 1A and 1B, sensing electrodes 22A and 22B are separated from one another by defibrillation electrode 20A. In other examples, however, sensing electrodes 22A and 22B may be both distal of defibrillation electrodes 20, or both proximal of defibrillation electrodes 20. In other examples, defibrillation lead 18A may include a greater number or a fewer number of electrodes at various locations proximal and/or distal to defibrillation electrodes 20. In these and/or other examples, ICD 10A may include one or more electrodes on another lead (not shown in FIGS. 1A-1C).

ICD system 4A may sense electrical signals via one or more sensing vectors that include combinations of electrodes 22A and 22B and the housing electrode of ICD 10A. For example, ICD 10A may obtain electrical signals that are sensed using a sensing vector between sensing electrodes 22A and 22B, obtain electrical signals sensed using a sensing vector between sensing electrode 22B and the conductive housing electrode of ICD 10A, obtain electrical signals sensed using a sensing vector between sensing electrode 22A and the conductive housing electrode of ICD 10A, or a combination thereof. In some instances, ICD 10A may sense cardiac electrical signals using a sensing vector that includes one of the defibrillation electrode sections 20A and 20B and one of sensing electrodes 22A and 22B or the housing electrode of ICD 10A.

The sensed electrical intrinsic signals include electrical signals that are generated by cardiac muscle and are indicative of depolarizations and repolarizations of heart 16A at various times during the cardiac cycle. The sensed electrical signals may also include electrical signals, e.g., pacing pulses, generated by PD 12A and delivered to heart 16A. ICD 10A analyzes the electrical signals sensed by the one or more sensing vectors to detect tachyarrhythmia, such as atrial tachycardia, atrial fibrillation, ventricular tachycardia, or ventricular fibrillation. In response to detecting the tachyarrhythmia, e.g., a ventricular fibrillation, ICD 10A may begin to charge a storage element, such as a bank of one or more capacitors. Upon determining that the storage element is sufficiently charged, ICD 10A may deliver one or more defibrillation pulses to certain chamber(s) of heart 16A via defibrillation electrodes 20 of defibrillation lead 18A, if ICD 10A determines that the tachyarrhythmia is still present.

In the example of FIG. 1A, PD 12A is implanted within the left ventricle of heart 16A, to provide pacing pulses to the left ventricle, e.g., for CRT. While illustrated as being implanted within the left ventricle as an example, it will be appreciated that PD 12A may be implanted at different positions as well. For instance, PD 12A may be implanted epicardially. That is, in accordance with epicardial implantation, PD 12A may be positioned externally to heart 16A and may be connected via one or more leads or in a leadless fashion to the left ventricle of heart 16A. In other examples, PD 12A or other PDs may be implanted within or externally to other chambers of heart 16A PD 12A may be constructed to have dimensions to fit within the available volume of the left ventricle of heart 16A and to be attachable to a wall, e.g., at or near the apex, of the left ventricle of heart 16A. A smaller size of PD 12A may also reduce the risk of thrombus forming in heart 16A. In some examples, PD 12A may leverage cardiac electrogram (EGM) sensing capabilities of ICD 10A, and therefore, may not include EGM sensing circuitry. As such, PD 12A may utilize a smaller capacity battery than in scenarios where regular EGM sensing for electrical cardiac events is performed.

For example, ICD 10A may be configured to sense electrical activity of heart 16A, such as atrial depolarizations or P-waves, and determine when PD 12A should deliver one or more pacing signals (e.g., pulses) to the left ventricle of heart 16A. ICD 10A may then transmit control signals to PD 12A to provide timing information associated with the pacing pulses that are to be delivered. The timing information may be determined based on one or more stored A-V or V-V intervals, which may be determined by processing circuitry, e.g., of ICD 10A and/or PD 12A, as described above. Upon receiving the control signals from ICD 10A, PD 12A may deliver the pacing signals or pulses according to the timing information indicated by the received control signals. ICD 10A and PD 12A may operate using transmission schedules and communication schedules to limit the amount of time that PD 12A operates communication circuitry that receives the control signals in a powered-on state.

In some examples, ICD 10A may also provide pacing signals as part of cardiac therapy using sensing electrodes 22A and/or 22B of defibrillation lead 18A. In other examples, ICD 10A may be coupled to one or more intracardiac leads carrying respective electrodes configured to be disposed within the right atrium and the right ventricle of heart 16A and deliver pacing pulses via these intracardiac leads as part of the cardiac therapy along with PD 12A. In other examples, additional PDs like PD 12A may be disposed within the right atrium and/or the right ventricle of heart 16A. Any PD(s) placed within the right atrium and/or right ventricle of heart 16A may be similarly controlled by ICM 10A. Alternatively, one or both PDs in the right atrium and/or right ventricle may provide control signals to PD 12A disposed in the left ventricle of heart 16A.

In another example, PD 12A implanted in the left ventricle and/or a PD implanted in the right ventricle or other heart chamber may be configured for cardiac sensing, delivering other pacing therapy, such as bradycardia pacing therapy, anti-tachycardia pacing (ATP), and/or post-shock pacing, to heart 16A, and/or detecting impingement between itself or other IMD and heart 16A or another structure. For example, PD 12A or a PD implanted in or on the right ventricle may deliver A-V synchronous bradycardia pacing therapy, timed relative to the atrial depolarization based on control signals received from ICD 10A in accordance with the techniques described herein.

Again, in some examples, PD 12A does not include EGM sensing circuitry. In other examples, PD 12A may be capable of sensing electrical signals using the electrodes carried on the housing of PD 12A. These electrical signals may be electrical signals generated by cardiac muscle and indicative of depolarizations (e.g., a ventricular depolarization or R-wave, or an atrial depolarization or P-wave) and repolarizations (e.g., a ventricular repolarization or T-wave) of heart 16A at various times during the cardiac cycle. PD 12A may analyze the sensed electrical signals to detect tachyarrhythmia, such as ventricular tachycardia or ventricular fibrillation, bradyarrhythmia, or even shocks. In response to detecting these conditions, PD 12A may, e.g., depending on the type of arrhythmia or shock, begin to deliver bradycardia pacing therapy, ATP, or post-shock pacing, with or without information from another device. In some examples, PD 12A may only detect arrhythmias in response to failing to detect control signals from ICM 10A for a predetermined period, or over a predetermined number of communication windows.

Figure 2:
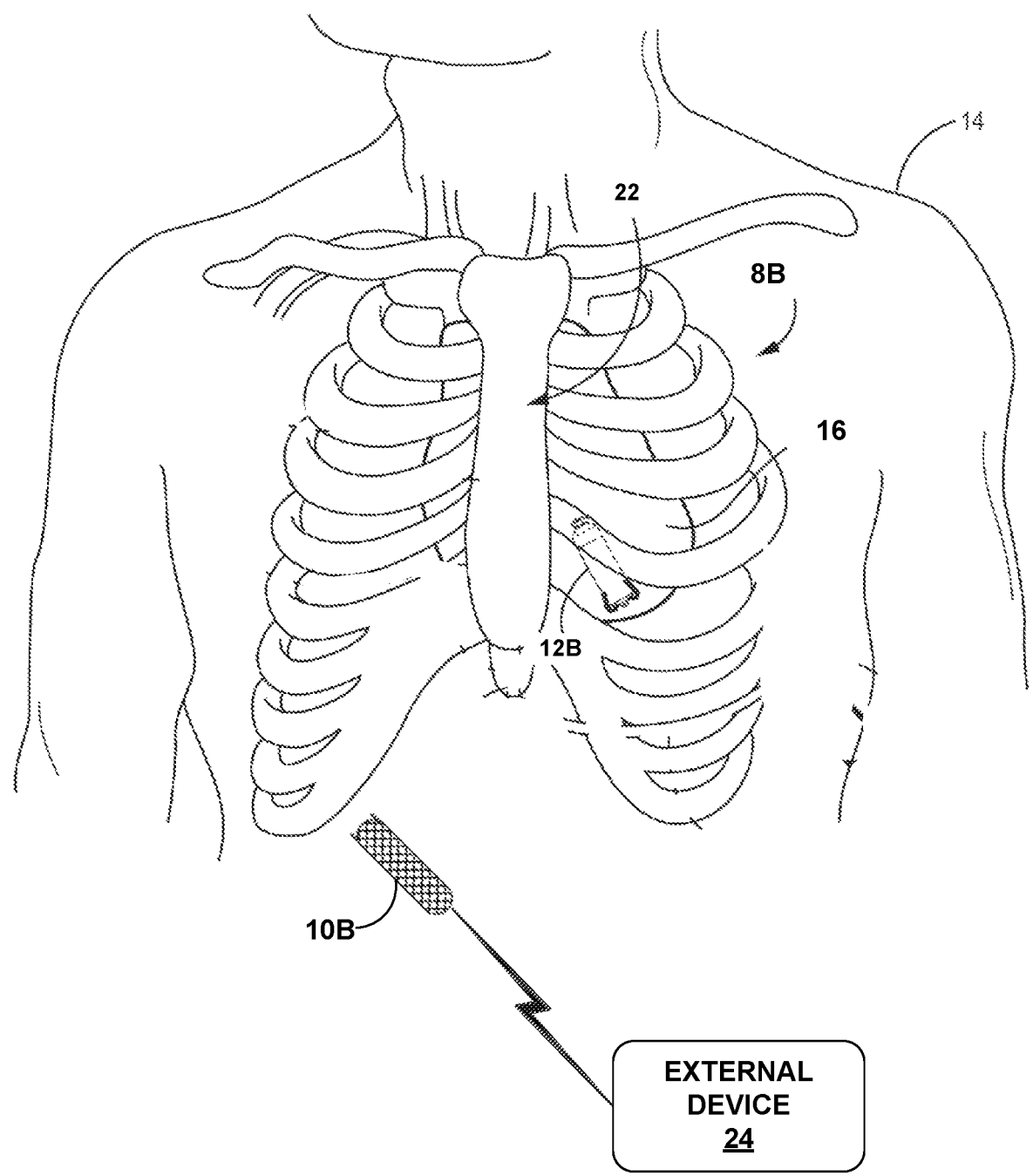
FIG. 2 is a conceptual diagram illustrating an example front view of a patient implanted with another example medical device system that includes an insertable cardiac monitoring (ICM) device that is inserted subcutaneously or substernally in the patient, and a PD implanted within a cardiac chamber of the patient, in accordance with one or more aspects of this disclosure.

Although FIGS. 1A-1C are illustrated and described in the context of a substernal ICD system 4A and a PD 12A, techniques in accordance with one or more aspects of the present disclosure may be applicable to other medical device systems. One example of another medical device system 8 that may implement the techniques of this disclosure is shown in FIG. 2 and discussed in further detail below with respect to FIG. 2. In another example, instead of an extravascular ICD (EV-ICD) system, a subcutaneous or submuscular pacing device coupled to a ventricular intracardiac lead may be implanted within the patient. In this manner, the pacing device may provide pacing pulses to the right ventricle of heart 16A via the intracardiac lead, and control PD 12A to provide pacing pulses to the left ventricle of heart 16A. In another example, a subcutaneous or submuscular pacing device coupled to a ventricular intracardiac lead carrying electrodes may be coupled to a motion sensor, e.g. by the lead, another lead, or wirelessly, and may implement the techniques of this disclosure for evaluating contractions to determine if impingement is occurring during cardiac therapy. As such, in some examples, the sensor may be included as a part of an endocardial lead, such as a left-endocardial lead. The examples of FIGS. 1A-1C and 2 are for illustrative purposes and should not be considered limiting of the techniques described herein, in any way.

External device 24 may be configured to communicate with ICD 10A and/or PD 12A. In examples where external device 24 only communicates with one of ICD 10A or PD 12A, the non-communicative device may receive instructions from or transmit data to the device in communication with external device 24. In some examples, external device 24 may include, be, or be part of one or more of a handheld computing device, a computer workstation, or a networked computing device. External device 24 may include a user interface that is configured or otherwise operable to receive input from a user. In other examples, external device 24 may process user interactions that are relayed remotely, such as via a networked computing device. External device 24 may process user interactions to enable users to communicate with PD 12A and/or ICD 10A. For example, external device 24 may process user inputs to send an interrogation request and retrieve therapy delivery data, to update therapy parameters that define therapy, to manage communication between PD 12A and/or ICD 10A, or to perform any other activities with respect to PD 12A and/or ICD 10A. Although the user is typically a physician, technician, surgeon, electrophysiologist, clinician, or other healthcare professional, the user may be patient 14 in some examples.

External device 24 may also allow the user to define how PD 12A and/or ICD 10A senses electrical signals (e.g., EGMs), detects arrhythmias (e.g., tachyarrhythmias), delivers therapy (e.g., CRT), and communicates with other devices of cardiac medical device system 8A. External device 24 may also allow the user to define how PD 12A and system 8A detect impingements of PD 12A by cardiac tissue. For example, external device 24 may be used to change tachyarrhythmia or impingement detection parameters, such as thresholds or other detection criteria.

The impingement detection parameters may be used by processing circuitry of system 8A, e.g., of ICD 10A, PD 12A, and/or external device 24, to identify impingements based on one or more characteristics of the signal during a cardiac cycle satisfying one or more criteria. The characteristics satisfying the criteria may include, for example, a frequency exceeding a threshold and/or a magnitude of motion orthogonal to a primary axis of systolic motion exceeding a threshold, as will be described in greater detail herein. External device 24 may also allow a user to program A-V and/or V-V intervals for cardiac therapy. For example, external device 24A may allow a user to select an A-V interval, and program ICD 10A to trigger PD 12A to deliver ventricular pacing pulse at certain time after a detected P-wave based on the selected A-V interval, or program PD 12A to deliver ventricular pacing pulse at a certain time after a trigger signal from ICD 10A based on the selected A-V interval.

External device 24 may take the form of an external programming device for one or both of ICD 10A and PD 12A. In some examples, external device 24 may additionally or alternatively include processing circuitry for performing, in whole or part, the impingement detection techniques of this disclosure, and/or include a user interface capable of indicating impingements or a degree of impingement to a user. In some examples, external device 24 may be present during implantation of PD 12A, e.g., in an operating or procedure room, and provide an indication of impingement, e.g., to an implanting physician, during implantation of PD 12A.

External device 24 may communicate with PD 12A and/or ICD system 4A via wireless communication using any techniques known in the art. Examples of communication techniques may include, for example, proprietary and nonproprietary radiofrequency (RF) telemetry, inductive telemetry, acoustics, and tissue conduction communication (TCC), but other techniques are also contemplated. During TCC, current is driven through the tissue between two or more electrodes of a transmitting device. The electrical signal spreads and may be detected at a distance by measuring the voltage generated between two electrodes of a receiving device.

In some examples, PD 12A and ICD 10A may engage in communication to facilitate the appropriate detection of impingement, detection of arrhythmias, and/or appropriate delivery of pacing therapy. The communication may include one-way communication in which one device is configured to transmit communication messages and the other device is configured to receive those messages according to the respective schedule. The communication may instead include two-way communication in which each device is configured to transmit and receive communication messages. Both of PD 12A and ICD 10A may be configured to toggle between one-way communication modes and two-way communication modes. The communication may be via TCC or other communication signals, e.g., RF communication signals.

FIG. 2 is a conceptual diagram illustrating an example front view of patient 14 implanted with another example medical device system 8B that includes an insertable cardiac monitoring (ICM) device 10B that is inserted subcutaneously or substernally in the patient, and PD 12B implanted either epicardially or within a cardiac chamber of patient 14, in accordance with one or more aspects of this disclosure. Components illustrated in FIG. 2 with like numbers of those of FIGS. 1A-1C may be similarly configured and may provide similar functionality to the similarly-numbered components illustrated in FIGS. 1A-1C. Medical device system 8B of FIG. 2 may leverage cardiac signal sensing capabilities of ICM 10B or PD 12B for collecting, measuring, and storing various forms of diagnostic data, including generating any corresponding reports or alerts. In certain cases, ICM 10B or PD 12B may directly analyze collected diagnostic data and generate any corresponding reports or alerts. In some cases, however, ICM 10B or PD 12B may send diagnostic data to external device 24. In some examples, ICM 10B may take the form of a Reveal LINQ™ ICM, available from Medtronic plc, of Dublin, Ireland.

Medical device system 8A of FIGS. 1A-1C and medical device system 8B of FIG. 2 may each be configured to detect and indicate impingement according to the techniques of this disclosure. As such, the impingement detection and reporting techniques of this disclosure are described hereinafter as being performed generically by "medical device system 8," and/or "PD 12," although it will be appreciated that the described techniques may be performed by the respective corresponding systems/devices illustrated in FIGS. 1A-1C or FIG. 2.

Medical device system 8 and/or components thereof may be configured to detect activity of heart 16, and deliver pacing therapy in a timed relationship to such activity based on a stored interval, e.g., an A-V or V-V interval. As described above, IMDs 10 may, in various examples, represent different types of cardiac monitoring (and in some cases therapy) devices that may be implanted substernally, subcutaneously, or elsewhere in the body of patient 14. In any of these implementations, IMD 10 includes interface hardware and sensing circuitry that senses a cardiac signal that varies as a function of a cardiac cycle of heart 16. For instance, the sensing circuitry of IMD 10 may detect an atrial and/or ventricular activation event based on the features of the signal during the cardiac cycle. IMD 10 may provide an indication to PD 12, such that PD 12 delivers ventricular pacing at the A-V or V-V interval after the event, in response to IMD detecting the activation event.

According to the techniques of this disclosure, a motion sensor within or coupled to PD 12, e.g., a three-dimensional accelerometer, may generate a signal that indicates motion of PD 12, including impingement of PD 12 with the heart or other structures. According to the techniques of this disclosure, processing circuitry, e.g., of PD 12, IMD 10, external device 24, and/or any device described herein, may identify impingements based on features of the motion signal during the cardiac cycle, e.g., that are not associated with non-impinged motion of PD 12 within the heart during the cardiac cycle. Reducing impingement between medical device systems 8A and 8B in general, and PD 12 in particular, and other structures may be desired.

The processing circuitry may also generate diagnostic information based on detected impingement, e.g., whether impingement is detected or the numbers of beats exhibiting impingement, which may be reported to a user. The diagnostic information may include values of one or more metrics indicating an amount of impingement, e.g., a percentage of beats where PD 12 has acceptable or unacceptable levels of impingement. Indicating impingement to a user may include a binary indication of whether or not impingement has occurred at a current implant location, or an amount of impingement, such as the aforementioned numbers or percentages, or impingement levels, e.g., high, medium, or low, which may be indicated by color, text, other graphics, or sound, and determined based on the aforementioned numbers or percentages. The indication of impingement may be provided via a user interface, such as external device 14 or another computing device. An implanting clinician may explant and/or change an implant location of PD 12 based on the indication of impingement.

Figure 3:
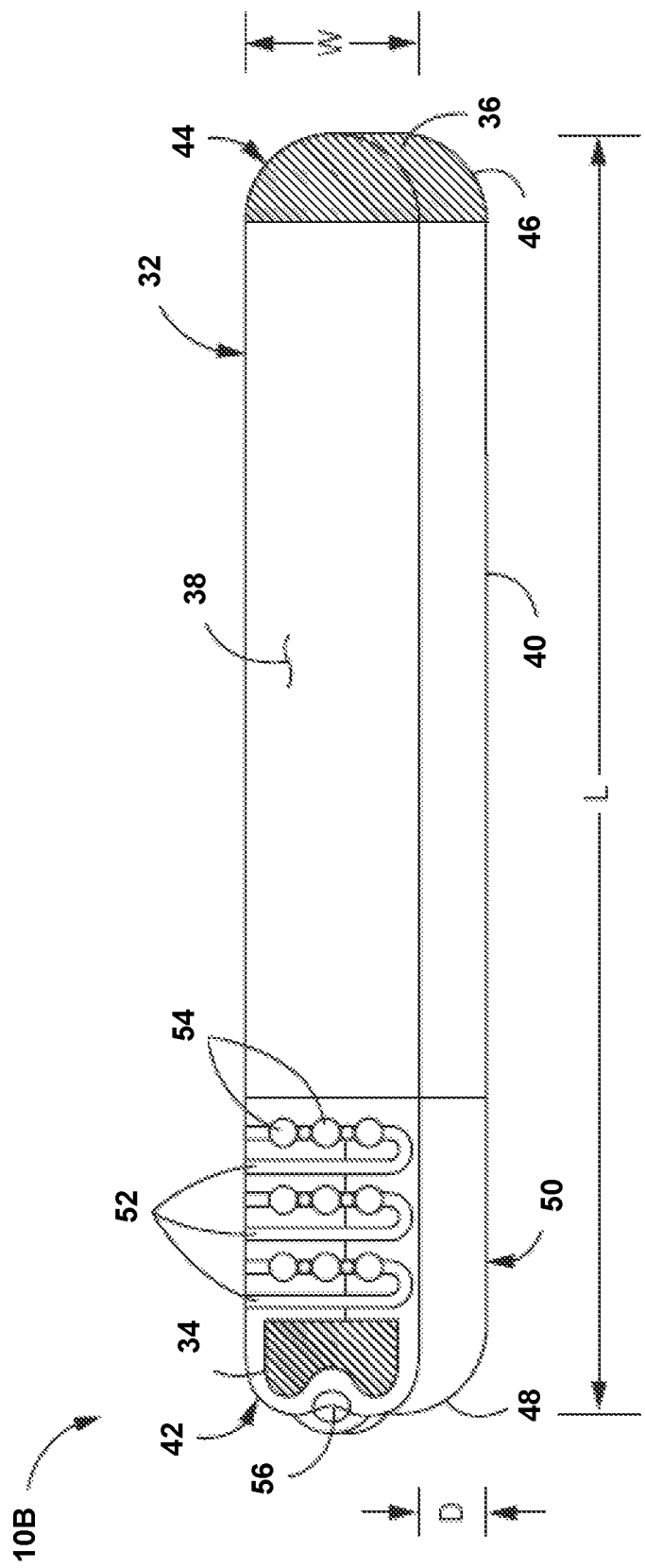
FIG. 3 is a conceptual drawing illustrating an example configuration of the ICM device illustrated in FIG. 2, in accordance with one or more aspects of this disclosure.

FIG. 3 is a conceptual drawing illustrating an example configuration of ICM 10B illustrated in FIG. 2. In the example shown in FIG. 3, ICM 10B may be embodied as a monitoring device having housing 32, proximal electrode 34 and distal electrode 36. Housing 32 may further include first major surface 38, second major surface 40, proximal end 42, and distal end 44. Housing 32 encloses electronic circuitry located inside the ICM 10B and protects the circuitry contained therein from body fluids. Electrical feedthroughs provide electrical connection of electrodes 34 and 36.

In the example shown in FIG. 3, ICM 10B is defined by a length L, a width W and thickness or depth D and is in the form of an elongated rectangular prism wherein the length L is much larger than the width W, which in turn is larger than the depth D. In one example, the geometry of the ICM 10B—a width W greater than the depth D—is selected to allow ICM 10B to be inserted under the skin of the patient using a minimally invasive procedure and to remain in the desired orientation during insertion. For example, the device shown in FIG. 3 includes radial asymmetries (notably, the rectangular shape) along the longitudinal axis that maintains the device in the proper orientation following insertion. For example, in one example the spacing between proximal electrode 34 and distal electrode 36 may range from thirty millimeters (mm) to fifty-five mm, thirty-five mm to fifty-five mm, and from forty mm to fifty-five mm and may be any range or individual spacing from twenty-five mm to sixty mm.

In addition, ICM 10B may have a length L that ranges from thirty mm to about seventy mm. In other examples, the length L may range from forty mm to sixty mm, forty-five mm to sixty mm and may be any length or range of lengths between about thirty mm and about seventy mm. In addition, the width W of major surface 38 may range from three mm to ten mm and may be any single or range of widths between three mm and ten mm. The thickness of depth D of ICM 10B may range from two mm to nine mm. In other examples, the depth D of ICM 10B may range from two mm to five mm and may be any single or range of depths from two mm to nine mm.

Furthermore, ICM 10B, according to an example of the present disclosure, has a geometry and size designed for ease of implant and patient comfort. Examples of ICM 10B described in this disclosure may have a volume of three cubic centimeters (cm) or less, one-and-a-half cubic cm or less or any volume between three and one-and-a-half cubic centimeters. In addition, in the example shown in FIG. 3, proximal end 42 and distal end 44 are rounded to reduce discomfort and irritation to surrounding tissue once inserted under the skin of the patient. In some examples, ICM 10B, including instrument and method for inserting ICM 10B, is configured as described, for example, in U.S. Patent Publication No. 2014/0276928, which is entitled, "SUBCUTANEOUS DELIVERY TOOL," and published on Sep. 18, 2014. U.S. Patent Publication No. 2014/0276928 to Vanderpool et al. is incorporated herein by reference in its entirety. In some examples, ICM 10B is configured as described, for example, in U.S. Patent Publication No. 2016/0310031, which is entitled, "METHOD AND APPARATUS FOR DETERMINING A PREMATURE VENTRICULAR CONTRACTION IN A MEDICAL MONITORING DEVICE," and published on Oct. 27, 2016. U.S. Patent Publication No. 2016/0310031 to Sarkar is incorporated herein by reference in its entirety.

In the example shown in FIG. 3, once inserted within the patient, the first major surface 38 faces outward toward the skin of the patient while the second major surface 40 is located opposite the first major surface 38. Consequently, the first and second major surfaces may face in directions along a sagittal axis of patient 14A (e.g., see FIG. 2), and this orientation may be consistently achieved upon implantation due to the dimensions of ICM 10B. Additionally, an accelerometer, or axis of an accelerometer, may be oriented along the sagittal axis.

Proximal electrode 34 and distal electrode 36 are used to sense cardiac signals, e.g., cardiac EGM signals, intra-thoracically or extra-thoracically, which may be sub-muscularly or subcutaneously. EGM signals may be stored in a memory of the ICM 10B, and EGM data may be transmitted via integrated antenna 52 to another medical device, which may be another implantable device or an external device, such as external device 14A. In some example, electrodes 34 and 36 may additionally or alternatively be used for sensing any bio-potential signal of interest, which may be, for example, any EGM, electroencephalogram (EEG), electromyogram (EMG), or a nerve signal, from any implanted location.

In the example shown in FIG. 3, proximal electrode 34 is close to the proximal end 42, and distal electrode 36 is close to distal end 44. In this example, distal electrode 36 is not limited to a flattened, outward facing surface. Distal electrode 36 may extend from first major surface 38 around rounded edges 46 and/or end surface 48 and onto the second major surface 40 so that the electrode 36 has a three-dimensional curved configuration. In the example shown in FIG. 3, proximal electrode 34 is located on first major surface 38 and is substantially flat, outward facing. However, in other examples, proximal electrode 34 may utilize the three-dimensional curved configuration illustrated with respect to distal electrode 36 in FIG. 3, providing a three-dimensional proximal electrode. In other examples still, distal electrode 36 may utilize a substantially flat, outward facing electrode located on first major surface 38 like that shown in FIG. 3 with respect to proximal electrode 34.

The various electrode configurations allow for configurations in which proximal electrode 34 and distal electrode 36 are located on both first major surface 38 and second major surface 40. In other configurations, such as the configuration shown in FIG. 3, only one of proximal electrode 34 or distal electrode 36 is located on both major surfaces 38 and 40. In still other configurations, both proximal electrode 34 and distal electrode 36 are located on one of the first major surface 38 or the second major surface 40 (i.e., proximal electrode 34 may be located on first major surface 38 while distal electrode 36 may be located on second major surface 40). In another example, ICM 10B may include electrodes on both major surface 38 and 40 at or near the proximal and distal ends of the device, such that a total of four electrodes are included on ICM 10B. Electrodes 34 and 36 may be formed of a plurality of different types of biocompatible conductive material, e.g., stainless steel, titanium, platinum, iridium, or alloys thereof, and may utilize one or more coatings such as titanium nitride or fractal titanium nitride.

In the example shown in FIG. 3, proximal end 42 includes a header assembly 50 that includes one or more of proximal electrode 34, integrated antenna 52, anti-migration projections 54, and/or suture hole 56. Integrated antenna 52 is located on the same major surface (i.e., first major surface 38) as proximal electrode 34 and is also included as part of header assembly 50. Integrated antenna 52 allows ICM 10B to transmit and/or receive data. In other examples, integrated antenna 52 may be formed on the opposite major surface as proximal electrode 34, or may be incorporated within the housing 32 of ICM 10B. In the example shown in FIG. 3, anti-migration projections 54 are located adjacent to integrated antenna 52 and protrude away from first major surface 38 to prevent longitudinal movement of the device. In the example shown in FIG. 3 anti-migration projections 54 includes a plurality (e.g., nine) small bumps or protrusions extending away from first major surface 38.

As discussed above, in other examples, anti-migration projections 54 may be located on the opposite major surface as proximal electrode 34 and/or integrated antenna 52. In addition, in the example shown in FIG. 3 header assembly 50 includes suture hole 56, which provides another means of securing ICM 10B to the patient to prevent movement following insert. In the example shown, suture hole 56 is located adjacent to proximal electrode 34. In one example, header assembly 50 is a molded header assembly made from a polymeric or plastic material, which may be integrated or separable from the main portion of ICM 10B.

Figure 4:
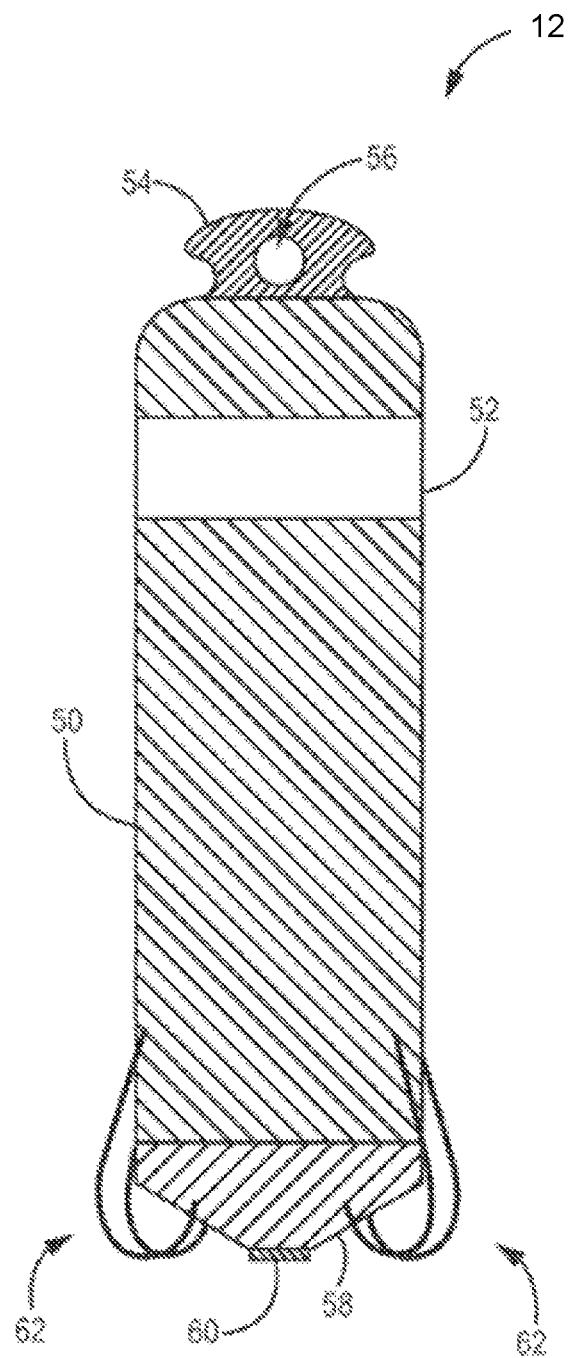
FIG. 4 is a conceptual drawing illustrating an example configuration of a PD in accordance with one or more aspects of this disclosure.

FIG. 4 is a conceptual drawing illustrating an example PD 12, which may correspond to either or both of PD 12A of FIG. 1A or PD 12B of FIG. 2. In addition, PD 12 may correspond to IMD 240 in FIGS. 11A-H. As shown in FIG. 4, PD 12 includes case 50, cap 58, electrode 60, electrode 52, fixation mechanisms 62, flange 54, and opening 56. Together, case 50 and cap 58 may be considered the housing of PD 12. In this manner, case 50 and cap 58 may enclose and protect the various electrical components within PD 12. Case 50 may enclose substantially all the electrical components, and cap 58 may seal case 50 and create the hermetically sealed housing of PD 12. Although PD 12 is generally described as including one or more electrodes, PD 12 may typically include at least two electrodes (e.g., electrodes 52 and 60) to deliver an electrical signal (e.g., therapy such as CRT) and/or provide at least one sensing vector. Electrodes 52 and 60 are carried on the housing created by case 50 and cap 58. In this manner, electrodes 52 and 60 may be considered leadless electrodes.

In the example of FIG. 4, electrode 60 is disposed on the exterior surface of cap 58. Electrode 60 may be a circular electrode positioned to contact cardiac tissue upon implantation. Electrode 52 may be a ring or cylindrical electrode disposed on the exterior surface of case 50. Both case 50 and cap 58 may be electrically insulating. Electrode 60 may be used as a cathode, and electrode 52 may be used as an anode, or vice versa, for delivering appropriate cardiac therapy (CRT, bradycardia pacing, ATP, post-shock pacing, etc.). However, electrodes 52 and 60 may be used in any stimulation configuration. In addition, electrodes 52 and 60 may be used to detect intrinsic electrical signals from cardiac muscle. In other examples, PD 12 may include three or more electrodes, where each electrode may deliver therapy and/or detect intrinsic signals. CRT and other pacing delivered by PD 12 may be "painless" to patient 14 or even undetectable by patient 14 since the electrical stimulation occurs very close to or at cardiac muscle and at relatively low energy levels compared with alternative devices.

Fixation mechanisms 62 may attach PD 12 to cardiac tissue. Fixation mechanisms 62 may be active fixation tines, screws, clamps, adhesive members, or any other types of attaching a device to tissue. As shown in the example of FIG. 4, fixation mechanisms 62 may be constructed of a memory material that retains a preformed shape. During implantation, fixation mechanisms 62 may be flexed forward to pierce tissue and allowed to flex back towards case 50. In this manner, fixation mechanisms 62 may be embedded within the target tissue.

Flange 54 may be provided on one end of case 50 to enable tethering or extraction of PD 12. For example, a suture or other device may be inserted around flange 54 and/or through opening 56 and attached to tissue. In this manner, flange 54 may provide a secondary attachment structure to tether or retain PD 12 within heart 16 if fixation mechanisms 62 fail. Flange 54 and/or opening 56 may also be used to extract PD 12 once the PD needs to be explanted (or removed) from patient 14 if such action is deemed necessary.

In another example, PD 12 may be configured to be implanted external to heart 16, e.g., near or attached to the epicardium of heart 16. An electrode carried by the housing of PD 12 may be placed in contact with the epicardium and/or one or more electrodes placed in contact with the epicardium at locations sufficient to provide an indication of impingement. In any example, IMD 10 may communicate with one or more leadless or leaded devices implanted internal or external to heart 16.

Figure 5:
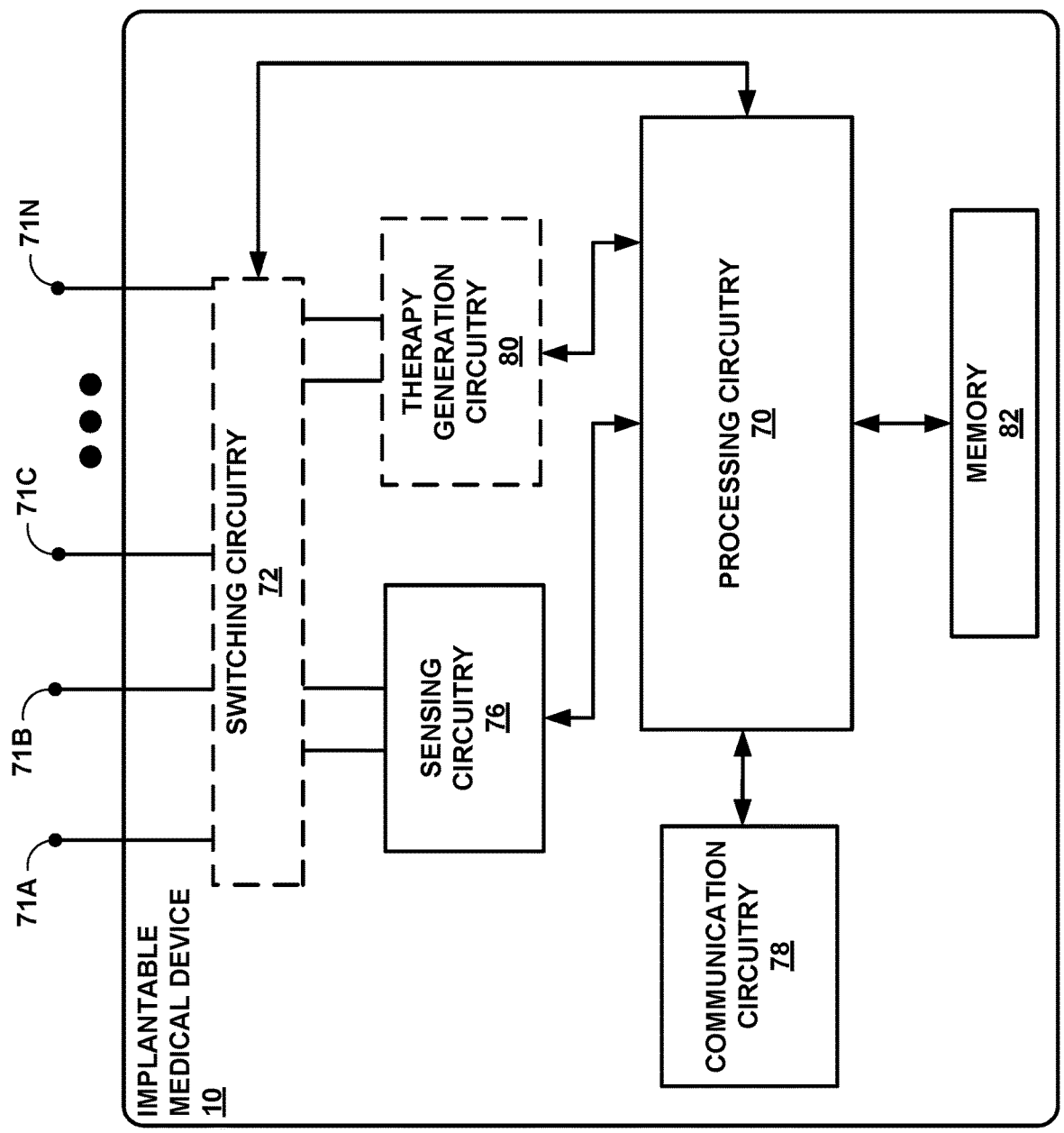
FIG. 5 is a functional block diagram illustrating an example configuration of an IMD in accordance with one or more aspects of this disclosure.

FIG. 5 is a block diagram of an example configuration of an IMD 10 that is configured according to one or more aspects of this disclosure. IMD 10 of FIG. 5 may, in various use case scenarios, represent an example of ICD 10A of FIGS. 1A-1C or ICM 10B of FIG. 2. IMD 10 includes two or more electrodes 71A-N (collectively "electrodes 71"), which may correspond to defibrillation electrodes 20 (FIGS. 1A-C), sensing electrodes 22 FIGS. 1A-C), one or more housing electrodes of ICD 10A (FIGS. 1A-C), or electrodes 34 and 36 (FIG. 3).

IMD 10 may include processing circuitry 70 for controlling sensing circuitry 76, communication circuitry 78, (optionally) switching circuitry 72, memory 82, and (option- ally) therapy generation circuitry 80. The optional nature of switching circuitry 72 and therapy generation circuitry 80 is shown using dashed-line borders to indicate the optional aspect, in FIG. 5. As one example, therapy generation circuitry 80 is indicated as optional because some embodiments of an IMD configured as an ICM do not deliver therapy. Switching circuitry 72 may include one or more switches, such as metal-oxide-semiconductor field-effect transistors (MOSFETs) or bipolar transistors. Processing circuitry 70 may control switching circuitry 72 to connect selected groupings of electrodes 71 to sensing circuitry 76 to sense one or more physiological electrical signals.

Sensing circuitry 76 is configured to receive cardiac electrical signals from selected combinations of two or more electrodes 71 and sense cardiac events attendant to depolarization and repolarization of cardiac tissue. Sensing circuitry 76 may include one or more sensing channels, each of which may be selectively coupled to respective combinations of electrodes 71 to detect electrical activity of a particular chamber of heart 16, e.g., one or more atrial and/or ventricular sensing channels. Each sensing channel may be configured to amplify, filter and rectify the cardiac electrical signal received from selected electrodes coupled to the respective sensing channel to detect cardiac events, e.g., P-wave and R-waves. For example, each sensing channel may include one or more filters and amplifiers for filtering and amplifying a signal received from a selected pair of electrodes. The resulting cardiac electrical signal may be passed to cardiac event detection circuitry that detects a cardiac event when the cardiac electrical signal crosses a sensing threshold. The cardiac event detection circuitry may include a rectifier, filter and/or amplifier, a sense amplifier, comparator, and/or analog-to-digital converter. Sensing circuitry 76 may output an indication to processing circuitry 70 in response to sensing a cardiac event in a chamber of interest, e.g., a P-wave or R-wave. In this manner, processing circuitry 70 may receive detected cardiac event signals corresponding to the occurrence of detected P-waves and R-waves. Indications of detected R-waves may be used by processing circuitry 70 for detecting ventricular arrhythmia episodes, and indications of detected P-waves may be used by processing circuitry 70 for detecting atrial arrhythmia episodes. Sensing circuitry 76 may also pass one or more digitized EGM signals to processing circuitry 70 for analysis, e.g., for use in cardiac rhythm discrimination and for morphological analysis.

Communication circuitry 78 may include circuitry for generating and modulating, and in some cases receiving and demodulating, continuous and/or pulsatile communication waveforms. Communication circuitry 78 may be configured to transmit and/or receive one or both of RF signals via an antenna (not shown) or TCC signals via electrodes 71. Although not shown in FIG. 5, communication circuitry 78 may be coupled to a selected two or more electrodes 71 via switching circuitry 72 for TCC.

In some examples, processing circuitry 70 may control switching circuitry 72 to connect electrodes 71 to therapy generation circuitry 80 to deliver a therapy pulse, such as a pacing, cardioversion, or defibrillation pulse to the heart. Therapy generation circuitry 80 is electrically coupleable to electrodes 71 and is configured to generate and deliver electrical therapy to heart 16 via selected combinations of electrodes 71. Therapy generation circuitry 80 may include charging circuitry, and one or more charge storage devices, such as one or more high voltage capacitors and/or one or more low voltage capacitors. Switching circuitry 72 may control when the capacitor(s) are discharged to selected combinations of electrodes 71. Therapy generation circuitry 80 and/or processing circuitry 70 may control the frequency, amplitude, and other characteristics of the therapy pulses. Therapy generation circuitry 80 may deliver the therapy pulses to electrodes 71 when switching circuitry 72 connects therapy generation circuitry 80 to electrodes 71.

Processing circuitry 70 may control switching circuitry 72 by sending control signals to the control terminals of one or more switches of switching circuitry 72. The control signals may control whether the switches of switching circuitry 72 conduct electricity between the load terminals of the switches. If switching circuitry 72 includes MOSFET switches, the control terminals may include gate terminals, and the load terminals may include drain terminals and source terminals.

Processing circuitry 70 may include various types of hardware, including one or more microprocessors, DSPs, ASICs, FPGAs, or any other equivalent integrated or discrete logic circuitry, as well as any combinations of such components. The term "processing circuitry" may generally refer to any of the foregoing logic circuitry, alone or in combination with other logic circuitry, or any other equivalent circuitry. Processing circuitry 70 represents hardware that may be configured to implement firmware and/or software that sets forth one or more of the algorithms described herein. Memory 82 includes computer-readable instructions that, when executed by processing circuitry 70, cause IMD 10 and processing circuitry 70 to perform various functions attributed to IMD 10 and processing circuitry 70 herein. Memory 82 may include any volatile, non-volatile, magnetic, optical, or electrical media, such as a random-access memory (RAM), read-only memory (ROM), non-volatile RAM (NVRAM), electrically-erasable programmable ROM (EEPROM), flash memory, or any other digital media.

In some examples, processing circuitry 70 receives indications of the occurrence of P-waves or other atrial events (or R-wave or other ventricular events) from sensing circuitry 76, or identifies the occurrence of P-waves or other atrial events by processing of a far-field EGM signal received from sensing circuitry using any of a variety of techniques known in the art. In response to the atrial or ventricular event, processing circuitry 70 may control communication circuitry 78 to transmit a signal to intracardiac PD 12. The signal causes intracardiac PD 12 to deliver a ventricular pacing pulse for cardiac therapy, absent an intrinsic ventricular depolarization prior to expiration of a timing interval, such as an A-V or V-V interval. As described above, one or both of IMD 10 and intracardiac PD 12 may store adjustable timing intervals that control the delivery of CRT based on an A-V interval or V-V interval. IMD 10 may store such intervals in memory 82.

In some examples, processing circuitry 70 of IMD 10 may receive a motion signal from a sensor of intracardiac PD 12. The motion sensor of intracardiac PD 12 may be configured to produce a signal that indicates motion of PD 12, e.g., motion of the housing of PD 12, including impingements of PD 12. Processing circuitry 70 may, according to the techniques described herein, detect impingements of PD 12 based on features of the signal from the sensor that indicates motion of PD 12. Processing circuitry 70 may identify one or more features of the signal during the cardiac contraction, determine whether the motion during the cardiac contraction indicates impingement based on the one or more features.

Processing circuitry 70 may additionally or alternatively receive a motion signal from the sensor of PD 12 that indicates mechanical activity of heart. Processing circuitry 70 may determine whether a contraction is fusion or not based on features of the cardiac contraction as indicated in the motion signal. Based on this evaluation of the contraction, processing circuitry 70 may control a timing interval stored in memory 82 and, for example, used by the processing circuitry to determine when to transmit a signal to PD 12 or when to instruct PD 12 to deliver a ventricular pacing pulse. Processing circuitry 70 may transmit a signal to intracardiac PD 12 via communication circuitry 78 to adjust a timing interval used by intracardiac PD 12. Techniques for adjusting therapy intervals based on evaluation of cardiac contraction are described, for example, in U.S. Provisional Patent Application Ser. No. 62/615,689 filed Jan. 10, 2018 and entitled "ADAPTIVE CARDIAC RESYNCHRONIZATION THERAPY," and U.S. Provisional Patent Application Ser. No. 62/615,703 filed Jan. 10, 2018 and entitled "CARDIAC RESYNCHRONIZATION THERAPY DIAGNOSTICS," both of which are herein incorporated by reference in their entirety.

Figure 6:
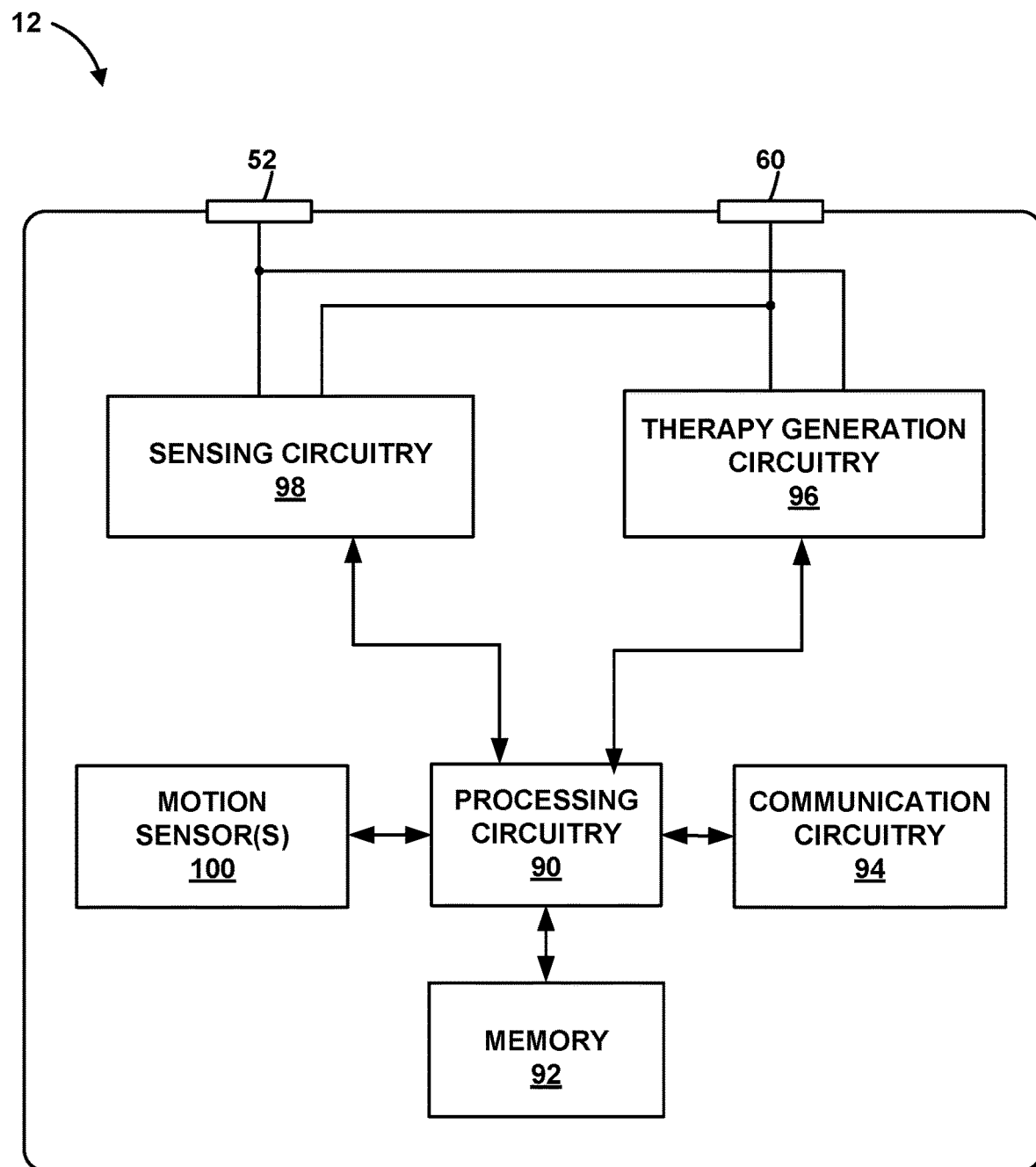
FIG. 6 is a functional block diagram illustrating an example configuration of a PD in accordance with one or more aspects of this disclosure.

FIG. 6 is a functional block diagram illustrating an example configuration of PD 12, which may correspond to PD 12A of FIGS. 1A-1C, PD 12B of FIG. 2, PD 12 of FIG. 4, and IMD 240 of FIGS. 9A-9H. In the illustrated example, PD 12 includes processing circuitry 90, memory 92, therapy generation circuitry 96, sensing circuitry 98, motion sensor 100, and communication circuitry 94. Memory 92 includes computer-readable instructions that, when executed by processing circuitry 90, cause PD 12 and processing circuitry 90 to perform various functions attributed to PD 12 and processing circuitry 90 herein (e.g., analyzing a motion signal from sensor 100 that indicates motion of the intracardiac PD and sensor 100 within the heart during contraction, and identifying impingements based on characteristics of the signal during a cardiac cycle, such as a frequency exceeding a threshold and/or a magnitude of motion orthogonal to a primary axis of systolic motion exceeding a threshold). Memory 92 may include any volatile, non-volatile, magnetic, optical, or electrical media, such as a random-access memory (RAM), read only memory (ROM), non-volatile RAM (NVRAM), electrically-erasable programmable ROM (EEPROM), flash memory, or any other digital or analog media.

Processing circuitry 90 may include any one or more of a microprocessor, a controller, a digital signal processor (DSP), an application specific integrated circuit (ASIC), a field-programmable gate array (FPGA), or equivalent discrete or analog logic circuitry. In some examples, processor 90 may include multiple components, such as any combination of one or more microprocessors, one or more controllers, one or more DSPs, one or more ASICs, or one or more FPGAs, as well as other discrete or integrated logic circuitry. The functions attributed to processing circuitry 90 herein may be embodied as software, firmware, hardware or any combination thereof.

Processing circuitry 90 controls therapy generation circuitry 96 to deliver stimulation therapy to heart 16 according to therapy parameters, which may be stored in memory 92. For example, processing circuitry 90 may control therapy generation circuitry 96 to deliver electrical pulses with the amplitudes, pulse widths, frequency, or electrode polarities specified by the therapy parameters. In this manner, therapy generation circuitry 96 may deliver pacing pulses to heart 16 via electrodes 52 and 60. Although PD 12 may only include two electrodes, e.g., electrodes 52 and 60, PD 12 may utilize three or more electrodes in other examples. PD 12 may use any combination of electrodes to deliver therapy and/or detect electrical signals from patient 14.

Therapy generation circuitry 96 is electrically coupled to electrodes 52 and 60 carried on the housing of PD 12. In the illustrated example, therapy generation circuitry 96 is configured to generate and deliver electrical stimulation therapy to heart 16. For example, therapy generation circuitry 96 may deliver pulses to a portion of cardiac muscle within heart 16 via electrodes 52 and 60. In some examples, therapy generation circuitry 96 may deliver pacing stimulation in the form of electrical pulses. In other examples, signal generator may deliver one or more of these types of stimulation in the form of other signals, such as sine waves, square waves, or other substantially continuous time signals. Therapy generation circuitry 96 may include charging circuitry, and one or more charge storage devices, such as one or more capacitors. Switching circuitry (not shown) may control when the capacitor(s) are discharged to electrodes 52 and 60.

Sensing circuitry 98 monitors signals from at least one of electrodes 52 and 60 to monitor electrical activity of heart 16, impedance, or another electrical phenomenon. Sensing may be done to determine heart rates or heart rate variability, or to detect ventricular dyssynchrony, arrhythmias (e.g., tachyarrhythmias) or other electrical signals. Sensing circuitry 98 may include switching circuitry to select the electrode polarity used to sense the heart activity. In examples with more than two electrodes, processing circuitry 90 may select the electrodes that function as sense electrodes, i.e., select the sensing configuration, via the switching circuitry within sensing circuitry 98. Sensing circuitry 98 may include one or more detection channels, each of which may be coupled to a selected electrode configuration for detection of cardiac signals via that electrode configuration. Some detection channels may be configured to detect cardiac events, such as R-waves, and provide indications of the occurrences of such events to processing circuitry 90, e.g., as described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety. Processing circuitry 90 may control the functionality of sensing circuitry 98 by providing signals via a data/address bus.

In addition to detecting and identifying specific types of cardiac rhythms), sensing circuitry 98 may also sample the detected intrinsic signals to generate an electrogram or other time-based indication of cardiac events. Processing circuitry 90 may also be able to coordinate the delivery of pacing pulses from different PDs, e.g., implanted in different chambers of heart 16, such as an PD implanted in the other ventricle. For example, processing circuitry 90 may identify delivered pulses from other PDs via sensing circuitry 98 and updating pulse timing. In other examples, PDs may communicate with each other via communication circuitry 94 and/or instructions over a carrier wave (such as a stimulation waveform).

Memory 92 may be configured to store a variety of operational parameters, therapy parameters, sensed and detected data, and any other information related to the therapy and treatment of patient 14. In the example of FIG. 6, memory 92 may store sensed EGMs, signals received from motion sensor 100 with features that may indicate impingement, communications from IMD 10, therapy parameter values, such as timing intervals that control the timing of cardiac therapy pacing pulses or other cardiac therapy control parameter values and values of one or more metrics that indicate cardiac therapy effectiveness. In some examples, memory 92 may act as a temporary buffer for storing data until it can be uploaded to IMD 10, another implanted device, or external device 24.

Motion sensor 100 may be contained within the housing of PD 12 and include one or more accelerometers, gyroscopes, electrical or magnetic field sensors, or other devices capable of detecting motion and/or position of PD 12. For example, motion sensor 100 may include a three-dimensional accelerometer that is configured to detect accelerations in any direction in space. Motion sensor 100 provides feedback about motion of PD 12, e.g., of the housing of PD 12. The motion indicated by sensor 100 may include motion of PD 12 due to the mechanical contraction pattern of the heart, including radial displacement and impingement of PD 12 with tissue. In this manner, motion sensor 100 may be used to detect PD 12 motion that may be indicative of cardiac events and/or noise.

For example, processing circuitry 90 may monitor the accelerations from motion sensor 100 to detect an impingement, e.g. collision, of PD 12 with another structure, such as cardiac tissue, another IMD, a component of another IMD, or a separated component of PD 12, such as a separated fixation mechanism. In some examples, during implant, e.g., during the process of checking initial pacing impedance and pacing thresholds at an implant location, PD 12 may monitor the motion signal throughout one or more cardiac cycles to determine if impingement is occurring. Detection of impingement at an implant location may prompt a clinician to change the implant location of PD 12. Since PD 12 may move with a chamber wall of heart 16, the detected changes in acceleration may also be indicative of contractions. Therefore, PD 12 may be configured to, based on the signal from sensor 100, identify heart rates and confirm ventricular dyssynchrony sensed via sensing circuitry 98.

As described in greater detail below, such as with respect to FIGS. 12A and 12B, the one or more features of the motion signal that may indicate impingement of PD 12 with cardiac tissue may comprise one or more of an amount or a direction of motion relative to a point of origin during the heartbeat. An amount of motion may be a distance relative to another point, such as an origin, or a velocity of the motion, e.g., an average or maximum velocity, in some examples. In some examples, the amount of motion is in at least one direction other than the primary axis of motion during the heartbeat, e.g., an amount of motion in at least one plane orthogonal to the primary axis of motion during the heartbeat.

During left-ventricular contraction of a relatively healthy heart, all left-ventricular walls shorten synchronously and with similar force. Such a contraction pulls the atrio-ventricular plane and the left-ventricular apex toward each other. The movement of the atrio-ventricular plane and the left-ventricular apex toward each other defines the primary axis of motion during the heartbeat. Further, in the case of a totally synchronous activation of all left-ventricular walls, there is a total force balance at the apex, and there is minimal or no resulting radial motion component at the apex that is associated with cardiac contraction.

In examples in which one or more sensor(s) 100 are other than an accelerometer, the features used to evaluate the motion signal using the techniques described herein may be the same or different than those provided by an accelerometer. For example, a gyroscope may provide rotational motion information different from that provided by accelerometers, but similar techniques may be used to evaluate the motion signal. For example, motion in directions, at frequencies, and/or having velocities other than those associated with cardiac contraction may be present in such signals and indicate impingement.

Motion sensor(s) 100 may be located at or near the apex of the heart, e.g., because PD 12 is implanted at that location. However, motion sensor(s) 100 may be implanted at other locations, e.g., on the ventricular free wall or septum. In either case, processing circuitry may detect motion in a direction other than the primary axis of motion during the cardiac contraction based on the signal from motion sensor(s) 100. Further, motion sensor(s) 100 may detect motion or displacement in any radial direction away from the origin point of the cardiac cycle. The x-axis and y-axis component of the radial displacement may be either determined individually for each x-axis and y-axis component or the combined vector length of the x-axis and y-axis component.

Techniques for evaluating the signal from motion sensor 100 to detect impingement may additionally or alternatively include comparing current signals from sensor 100, or values derived from the current signal, to template or baseline signals or values. Based on the comparison, processing circuitry may determine differences between the signal and the template, which may be compared to thresholds to determine whether the signal "matches" the template, e.g., is sufficiently similar to the template. The one or more templates may be stored in memory 92 (or another memory of system 8). The one or more templates may be generated by processing circuitry 90 or other processing circuitry based on the motion signal during one or more previous beats of known classification (such as by averaging the signal for a plurality of known beats of a given classification), either of the particular patient, or from a population of one or more similar patients. The one or more templates may include one or more of a template with acceptable level of impingement and a template with an unacceptable level of impingement, and processing circuitry may characterize a given signal as one with or not with an acceptable level of impingement based on whose template the signal best matches.

Further, the templates need not take the form of one or more substantially continuous-time signals, representing a number of values, from one or more sensors during a heartbeat (or portion of such a signal). Rather, a template may take the form of a template value for any one or more of the signal features disclosed herein, e.g., frequency or motion orthogonal to the primary axis of contraction. The template value may be, but need not necessarily be, determined based on a template signal or otherwise determined from motion signals of known classification (such as by averaging the signal for a plurality of known beats of a given classification), either of the particular patient, or from a population of one or more similar patients. Template values may include, as examples, values of: an amplitude of the signal during the heartbeat, a frequency of the signal during the heartbeat, a duration of the signal during the heartbeat, a maximum of the signal during the heartbeat, a minimum of the signal during the heartbeat, a rate of change of the signal during the heartbeat, a ratio of the maximum and the minimum during the heartbeat, a polarity of the signal during the heartbeat, or an amount of motion in one or more particular directions, such as orthogonal to the primary axis of motion during the heartbeat. Again, an amount of motion may be a displacement or velocity, as examples. The templates may include template values for multiple signal features. Although described in the context of processing circuitry 90 of intracardiac PD 12, processing circuitry of any one or more devices described herein may similarly use templates to identify impingement.

Communication circuitry 94 includes any suitable hardware, firmware, software or any combination thereof for communicating with another device, such as external device 24 or IMD 10, via TCC or RF signals, as described herein. In some examples, communication circuitry 94 may be configured for TCC communication with IMD 10 via electrodes 52 and 60. PD 12 may communicate with external device 24 via IMD 10, or communication circuitry 94 may be configured for RF communication with external device 24, e.g., via an antenna. In some examples, PD 12 may signal external device 24 to further communicate with and pass the alert through a network such as the Medtronic CareLink® Network developed by Medtronic plc of Dublin, Ireland, or some other network linking patient 14 to a clinician. PD 12 may spontaneously transmit information to the network or in response to an interrogation request from a user.

Figure 7:
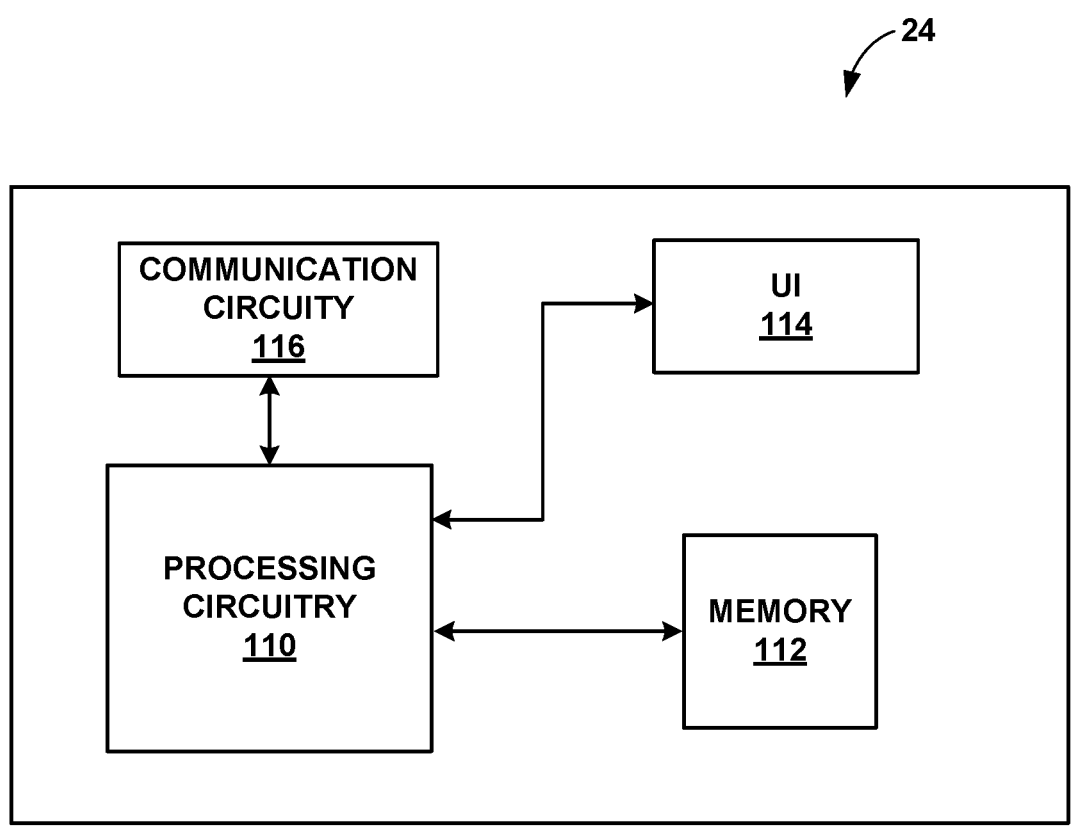
FIG. 7 is a functional block diagram illustrating an example configuration of the external device in FIG. 1A, in accordance with one or more aspects of this disclosure.

FIG. 7 is a functional block diagram illustrating an example configuration of external device 24. As shown in FIG. 7, external device 24 may include processing circuitry 110, memory 112, user interface 114, and communication circuitry 116. External device 24 may be a dedicated hardware device with dedicated software for communication with, e.g., programming of, PD 12 and/or IMD 10. Alternatively, external device 24 may be an off-the-shelf computing device running an application that enables external device 24 to program and/or otherwise communicate with PD 12 and/or IMD 10.

A user may use external device 24 to configure the operational parameters of and retrieve data from PD 12 and/or IMD 10. In one example, external device 24 may communicate directly to both PD 12 and IMD 10. In other examples, external device 24 may communicate to one of PD 12 and IMD 10, and that device may relay any instructions or information to or from the other device. The clinician may interact with external device 24 via user interface 114, which may include display to present graphical user interface to a user, and a keypad or another mechanism for receiving input from a user. In addition, the user may receive an alert or notification from IMD 10 indicating that a shock has been delivered, any other therapy has been delivered, or any problems or issues related to the treatment of patient 14.

Processing circuitry 110 may take the form one or more microprocessors, DSPs, ASICs, FPGAs, programmable logic circuitry, or the like, and the functions attributed to processing circuitry 110 herein may be embodied as hardware, firmware, software or any combination thereof. Memory 112 may store instructions that cause processing circuitry 110 to provide the functionality ascribed to external device 24 herein, and information used by processing circuitry 110 to provide the functionality ascribed to external device 24 herein. Memory 112 may include any fixed or removable magnetic, optical, or electrical media, such as RAM, ROM, CD-ROM, hard or floppy magnetic disks, EEPROM, or the like. Memory 112 may also include a removable memory portion that may be used to provide memory updates or increases in memory capacities. A removable memory may also allow patient data to be easily transferred to another computing device, or to be removed before external device 24 is used to program therapy for another patient.

External device 24 may communicate wirelessly with PD 12 and/or IMD 10, such as using RF communication or proximal inductive interaction. This wireless communication is possible with communication circuitry 116, which may be coupled to an internal antenna or an external antenna. An external antenna that is coupled to external device 24 may correspond to the programming head that may be placed over heart 16 or the location of the intend implant, as described above with reference to FIG. 1. Communication circuitry 116 may be configured with circuitry like communication circuitry 78 of FIG. 5.

Communication circuitry 116 may also be configured to communicate with another computing device via wireless communication techniques, or direct communication through a wired connection. Examples of local wireless communication techniques that may be employed to facilitate communication between external device 24 and another computing device include RF communication according to the 802.11 or Bluetooth specification sets, infrared communication, e.g., according to the IrDA standard, or other standard or proprietary telemetry protocols. An additional computing device in communication with external device 24 may be a networked device such as a server capable of processing information retrieved from IMD 10 and/or PD 12.

In some examples, processing circuitry 110 may receive a signal from sensor 100 of PD 12 via direct or indirect communication with PD 12 using communication circuitry 116. Using the signal, processing circuitry 110 may, in whole or in part, perform any of the methods described herein for detecting impingement. In some examples, processing circuitry 110 may receive values for features of the signal during one or more cardiac cycles rather than the motion signal, or classification of beats as to whether or not they include impingement rather than the feature values, and perform some portions of methods described herein using the received features or classification information. Features of a signal that may indicate impingement include an amount of motion (e.g., a maximum, mean, median, derivative or rate of change, or integral) during the cardiac cycle, which may be in one or more directions other than the primary axis of motion of the cardiac contraction, duration of the signal during the heartbeat, and signal hull curve or other morphological characterization of the signal. Features of the signal that may indicate impingement may additionally or alternatively include the presence of frequencies higher than those associated with movement of heart tissue during contraction. Impingement may be detected based on the frequency of the signal by determining that a magnitude of the signal at a particular frequency or within a particular frequency band, such as a range from about 10 Hertz (Hz) to about 100 Hz or more particularly from about 20 Hz to 50 Hz, satisfies, e.g., exceeds, a threshold.

Figure 8:
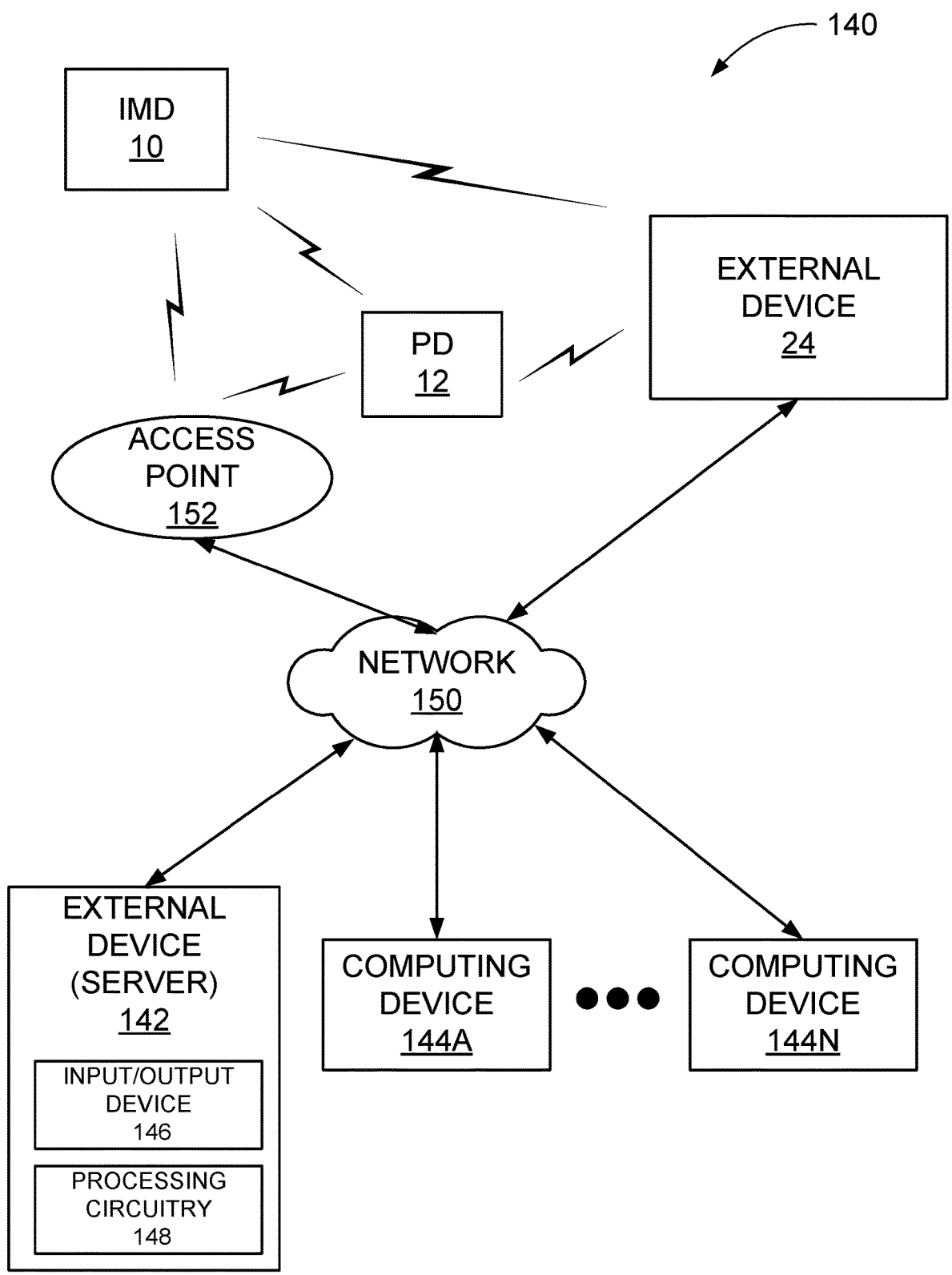
FIG. 8 is a block diagram illustrating a system that includes an external device, such as a server, and one or more computing devices that are coupled to an IMD, PD, and external device via a network, in accordance with one or more aspects of this disclosure.

FIG. 8 is a block diagram illustrating a system 140 that includes an external device 142, such as a server, and one or more computing devices 144A-144N that are coupled to IMD 10, PD 12, and external device 24 via a network 150, according to one example. In this example, IMD 10 uses communication circuitry to communicate with external device 24 via a first wireless connection and communicates with an access point 152 via a second wireless connection. PD 12 uses communication circuitry to communicate with external device 24 via a first wireless connection and communicates with an access point 152 via a second wireless connection. IMD 10 and PD 12 communicate with each other via a shared third wireless connection. In the example of FIG. 8, access point 152, external device 24, external device 142, and computing devices 144A-144N are interconnected, and able to communicate with each other, through network 150. In some cases, one or more of access point 152, external device 24, external device 142, and computing devices 144A-144N may be coupled to network 150 through one or more wireless connections. IMD 10, PD 12, external device 24, external device 152, and computing devices 144A-144N may each comprise one or more processing circuitries, such as one or more microprocessors, DSPs, ASICs, FPGAs, programmable logic circuitry, or the like, that may perform various functions and operations, such as those described herein.

Access point 152 may comprise a device that connects to network 150 via any of a variety of connections, such as telephone dial-up, digital subscriber line (DSL), or cable modem connections. In other examples, access point 152 may be coupled to network 150 through different forms of connections, including wired or wireless connections. In some examples, access point 152 may communicate with external device 24, PD 12, and/or IMD 10. Access point 152 may be co-located with patient 14 (e.g., within the same room or within the same site as patient 14) or may be remotely located from patient 14. For example, access point 152 may be a home monitor located in the patient's home or is portable for carrying with patient 14.

During operation, IMD 10 and/or PD 12 may collect, measure, and store various forms of diagnostic data. For example, IMD 10 and/or PD 12 may collect EGM and motion signals, and determine different CRT configurations, A-V intervals, and whether impingement is occurring. In certain cases, IMD 10 and/or PD 12 may directly analyze collected diagnostic data and generate any corresponding reports or alerts. In some cases, however, IMD 10 and/or PD 12 may send diagnostic data to external device 24, access point 152, and/or external device 142, either wirelessly or via access point 152 and network 150, for remote processing and analysis. For example, IMD 10 and/or PD 12 may send external device 24 data that indicates the occurrence and severity of impingement of cardiac tissue with PD 12, such as mechanical collisions with cardiac structures such as papillary muscles, cordae, valve structures, or ventricular endocardium. External device 24 may generate reports or alerts after analyzing the data.

In another example, IMD 10 and/or PD 12 may provide external device 142 with collected EGM and motion signal data, system integrity indications, and any other relevant physiological or system data via access point 152 and network 150. External device 142 includes one or more processing circuitries 148. In some cases, external device 142 may request such data, and in some cases, IMD 10 and/or PD 12 may automatically or periodically provide such data to external device 142.

In one example, external device 142 may comprise a secure storage site for information that has been collected from IMD 10, PD 12, and/or external device 24. In this example, network 150 may comprise an Internet network; and trained professionals, such as clinicians, may use computing devices 144A-144N to securely access stored data on external device 142. For example, the trained professionals may need to enter usernames and passwords to access the stored information on external device 142. In one embodiment, external device 142 may be a Medtronic CareLink® server provided by Medtronic plc of Dublin, Ireland. In some examples, patients may use computing devices 144 to receive data regarding their devices and treatment.

In some examples, processing circuitry and memory of one or more of access point 152, server 142, or computing devices 144, e.g., processing circuitry 148 and memory of server 142, may be configured to provide some or all the functionality ascribed to processing circuitry and memory of IMD 10 and/or PD 12. For example, server 142 may be configured to receive a signal from sensor 100 of PD 12 via communication with PD 12 via network 150 and one or more of access point 152 and external device 234. Using the signal, processing circuitry 146 may, in whole or in part, perform any of the methods described herein including detecting impingement based on the signal FIGS. 9A-H illustrate example techniques for securing PD 240 to patient tissue 200 using delivery device 220. PD 240 may correspond to PDs 12 in FIGS. 1A-1C, 2, 4, and 6. PDs 12 and 240 may be examples of IMDs that include a motion sensor and are configured for implantation on or within the heart. In some examples, delivery device 220 may be a catheter. As an example, patient tissue 200 may be a heart tissue, such as the inner wall of the left ventricle. For simplicity, a set of only two active fixation tines 210 are shown in each of FIGS. 9A-H but more fixation tines 210 may be used.

Figure 9A:
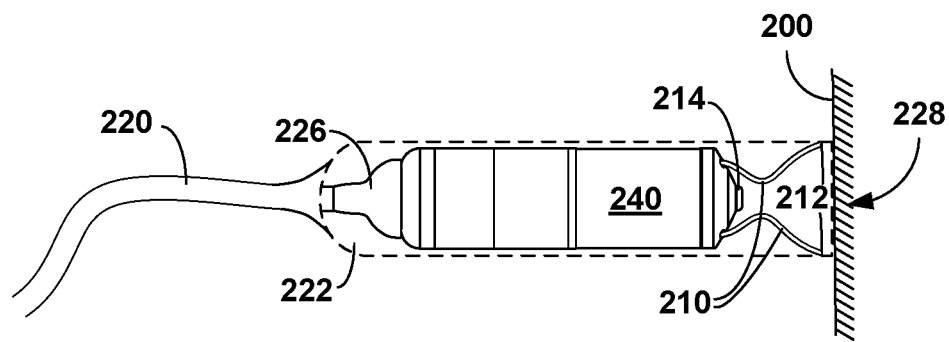
FIGS. 9A-H illustrate techniques for securing an IMD to a patient tissue, in accordance with one or more aspects of this disclosure.

FIG. 9A illustrates PD 240 within lumen 222 of delivery device 220. Lumen 222 holds active fixation tines 210 in a spring-loaded position in which distal ends 212 of active fixation tines 210 point away from PD 240. Aperture 228 is positioned adjacent patient tissue 200.

Figure 9B:
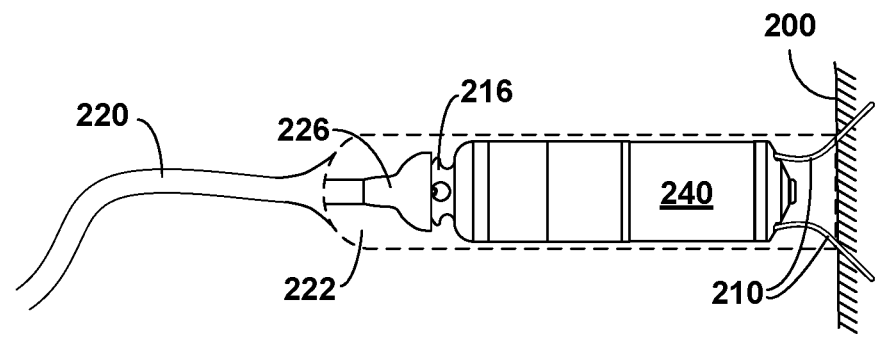
Figure 9C:
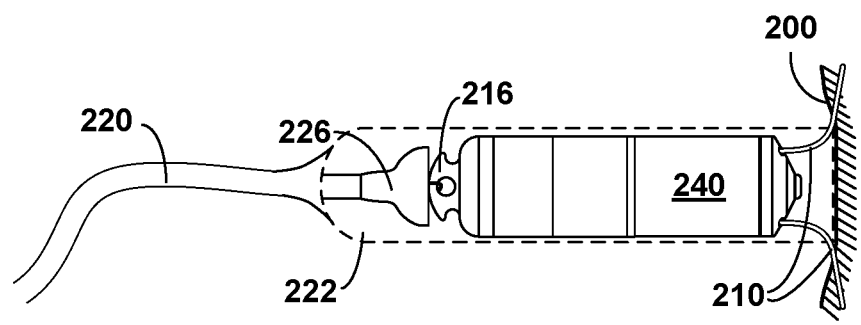

FIG. 9B illustrates PD 240 shortly after a clinician remotely activated active fixation tines 210 using deployment element 226 by pressing on plunger (not shown, proximal end of delivery device 220). As the clinician pressed plunger, deployment element 226 pushed PD 240 distally within lumen 222. Once the distal ends 212 of active fixation tines 210 reached aperture 228, active fixation tines 210 began to pull PD 240 out of lumen 222 via aperture 228. Distal ends 212 of active fixation tines 210 then penetrated patient tissue 200. FIG. 9B illustrates active fixation tines 210 in a position after distal ends 212 of active fixation tines 210 penetrated patient tissue 200 and shortly after beginning the transition from a spring-loaded position to a hooked position.

Figure 9D:
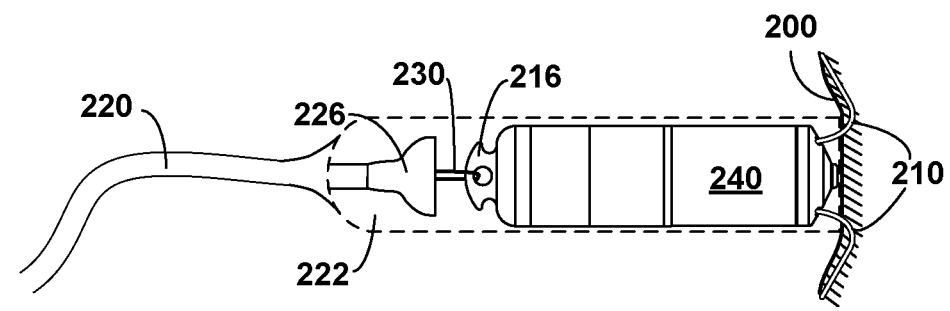
Figure 9E:
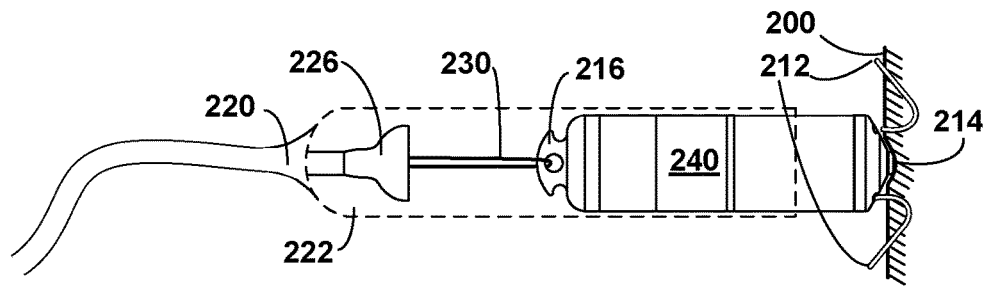
Figure 9F:
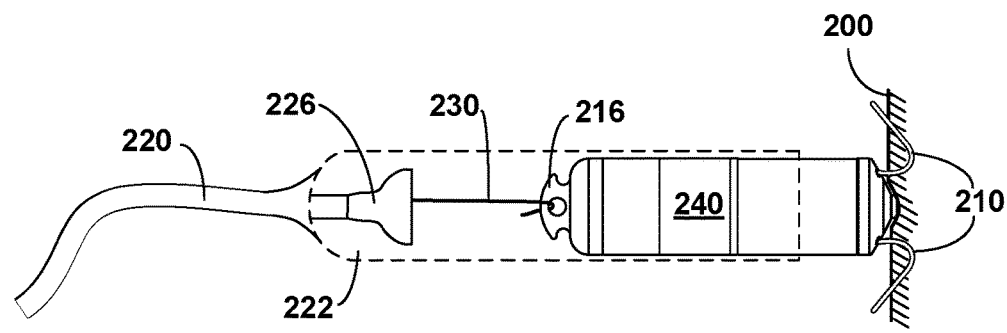

FIGS. 9B-F illustrate active fixation tines 210 as they move from a spring-loaded position in which distal ends 212 of active fixation tines 210 point away from PD 240 to a hooked position in which distal ends 212 of active fixation tines 210 bend back towards PD 240. FIGS. 9D-F illustrate active fixation tines 210 in hooked positions. In FIG. 9D, distal ends 212 of active fixation tines 210 remain embedded in patient tissue 200, whereas FIGS. 9E and 9F illustrate distal ends 212 of active fixation tines 210 penetrating out of patient tissue 200.

As active fixation tines 210 pull PD 240 from lumen 222, tether 230, which is attached to delivery tool interface 216 of PD 240 is exposed, e.g., as shown in FIG. 9E. Following deployment of PD 240, a clinician may remotely pull PD 240 back into lumen 222 by pulling on tether 230 at the proximal end of delivery device 220. For example, the clinician may direct PD 240 to perform a test to evaluate a performance characteristic of electrode 214 while PD 240 is secured to patient tissue 200 as shown in FIG. 9E. If the test of PD 240 indicates inadequate performance, the clinician may decide to redeploy, e.g., move, PD 240. Pulling PD 240 back into lumen 222 releases PD 240 from patient tissue 200 and returns PD 240 to the position shown in FIG. 9A. From this position, a clinician may reposition PD 240 as desired and redeploy PD 240. The performance test may include one or both of PD 240 measuring an impedance of an electrical path including electrode 214 or determining whether pacing pulses delivered by electrode 214 capture cardiac tissue 228.

As discussed herein, PD 240 may also determine whether impingements of PD 240 with cardiac tissue occur, e.g., during the implantation of PD 240 illustrated in FIGS. 9A-9H. In some examples, PD 240 may determine whether impingements occur while PD 240 is in the position illustrated by FIG. 9E, e.g., before, after, or concurrent with the performance testing of electrode 214. When PD 240 is in the proposed implant position as illustrated by FIG. 9E, a user, such as an implanting clinician or assistant, may direct PD 240 to execute the performance tests and check for impingements using external device 24 or another computing device. External device 24 or another computing device may provide the user an indication of the result of such tests, e.g., an indication of whether impingement occurred, or a degree of impingement. The user may determine whether to reposition PD 240 based on the indication.

Figure 9G:
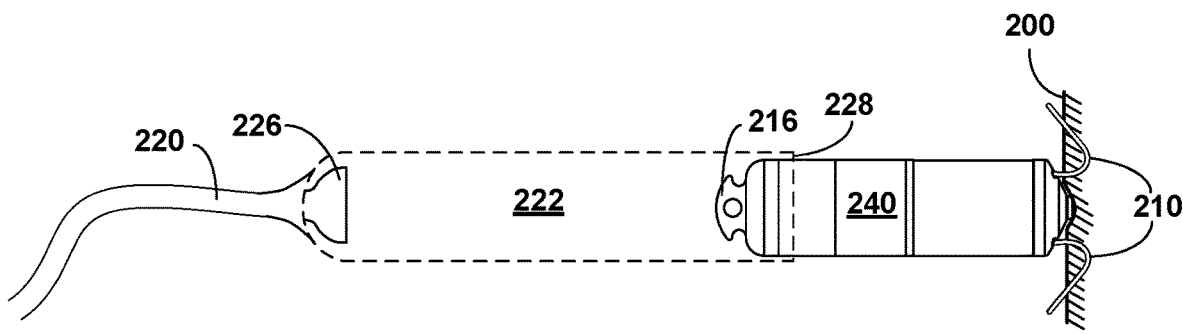
Figure 9H:
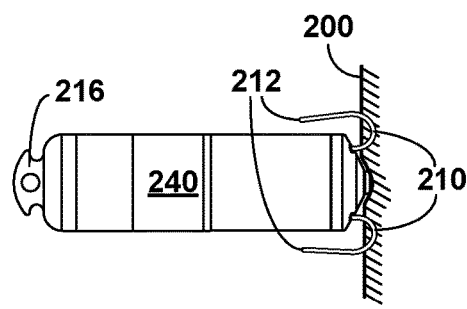

As shown in FIG. 9F, once PD 240 is secured to patient tissue 200 in the desired position, the clinician may release PD 240 from tether 230. For example, the clinician may sever tether 230 at the proximal end of delivery device 220 and remove tether 230 from delivery tool interface 216 by pulling on one of the severed ends of tether 230. As shown in FIG. 9G, once PD 240 is released from tether 230, the clinician may remove delivery device 220, leaving PD 240 secured to patient tissue 200. As shown in FIG. 9H, active fixation tines 210 may continue to migrate to a lower potential energy hooked position over time. Any of the hooked positions of active fixation tines 210 as shown in FIGS. 9D-G may be sufficient to adequately secure PD 240 to patient tissue 200.

While the techniques of FIGS. 9A-H are illustrated with respect to PD 240, the techniques may also be applied to a different IMD, such as a medical lead including a set of active fixation tines like medical leads. For example, such a medical lead may extend through a catheter during an implantation procedure. As such, deploying a medical lead may not require a separate deployment element within the catheter. Instead, pushing on the medical lead at the proximal end of the catheter may initiate deployment of a set of active fixation tines at the distal end of the medical lead by pushing the active fixation tines attached to the distal end of the medical lead out of the distal end of the catheter. Similarly, retracting a medical lead for redeployment may not require a tether, but may instead involve pulling on the medical lead at the proximal end of the catheter.

Figure 10:
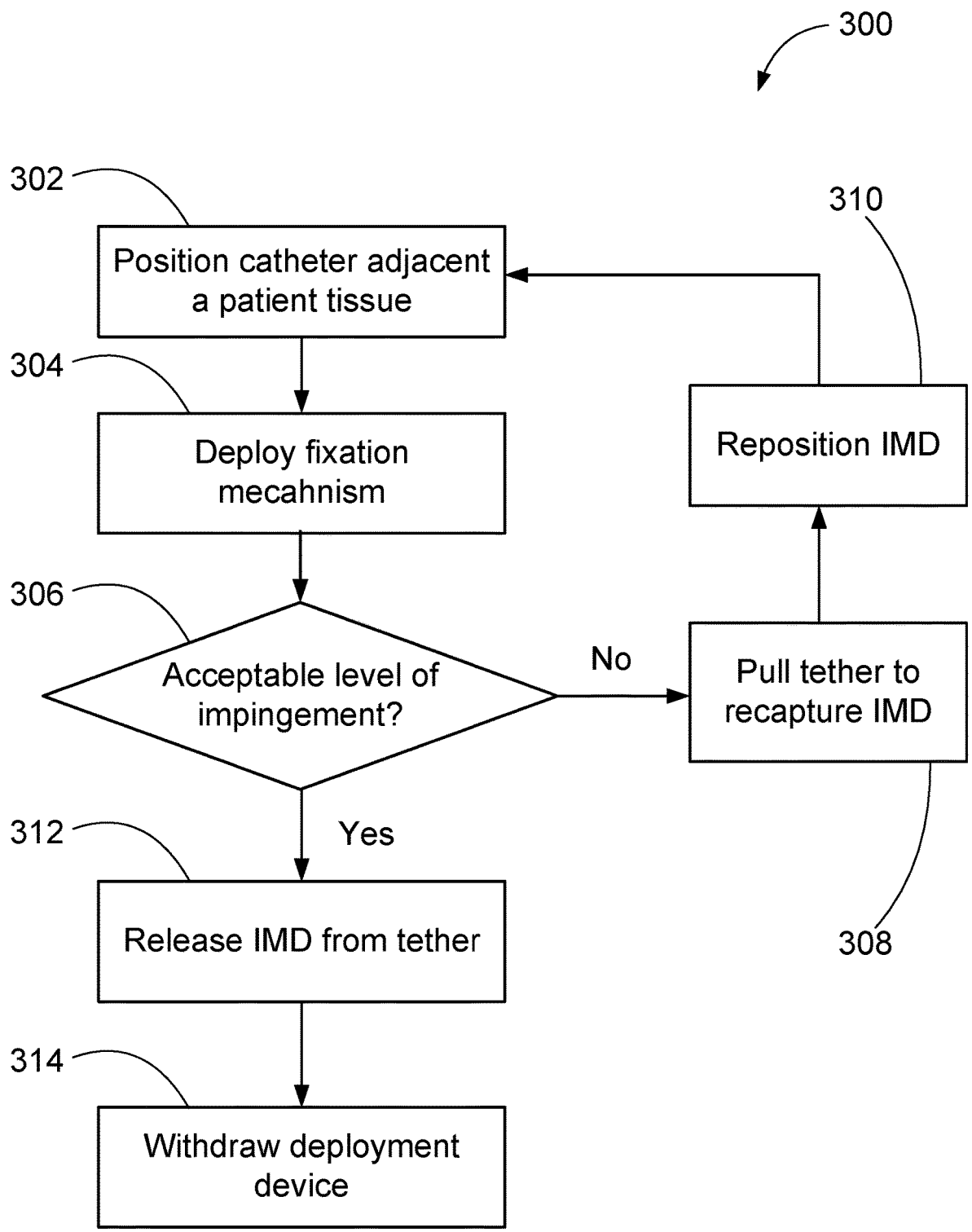
FIG. 10 is a flow diagram illustrating an example process of attaching an IMD to a patient tissue while monitoring impingement, in accordance with one or more aspects of this disclosure.

FIG. 10 is a flow diagram illustrating an example process for monitoring for impingement of an IMD within a patient including while implanting the IMD, in accordance with one or more aspects of this disclosure. More particularly, FIG. 10 illustrates method 300 in which PD 12 and/or processing circuitry of other devices of a medical device system 8, monitors for impingement of PD 12, e.g., with cardiac tissue present in a patient.

Method 300 begins during implantation of PD 12 or after PD 12 is implanted into the patient. Method 300 is not limited to the examples in which PD 12 is affixed to an inner wall of the left ventricle. For example, the fixation mechanism of PD 12 may be attached to the RV instead of the LV. Additionally, PD 12 may be placed on an outer wall of the LV and/or RV. Furthermore, although described in the context of an example in which PD 12 and processing circuitry 90 of PD 12 perform a number of the functions illustrated in the example of FIG. 10, in other examples one or more of these functions may be performed by one or more other devices that communicate with PD 12, such as IMD 10, external device 24, external device 142, or computing devices 144, e.g., by the processing circuitry of such devices.

According to example method 300, a catheter, which may include PD 12 within its lumen, is positioned to a location within the patient adjacent a patient tissue, such as a LV (302). Next, PD 12 is deployed from the catheter to the location within the patient, such as LV (304). For example, the clinician may push on the plunger (e.g., as illustrated with respect to FIG. 9B-9E) to deploy PD 12. The clinician and/or processing circuitry may then evaluate whether PD 12 is adequately fixated and positioned within the patient.

The evaluation may include determining whether a level of impingement between PD 12 and cardiac tissue or other structures, such as another PD or other IMD, or a component of PD 12 or another IMD, is acceptable (306). In order to determine whether there is an acceptable level of impingement, a motion signal may be received by processing circuitry 90 of PD 12 from sensor 100, which may be an accelerometer or gyroscope, as examples. Again, as discussed herein, the motion signal may additionally or alternatively be received by processing circuitry of other devices, including but not limited to IMD 10, external device 24, external device 142, and computing devices 144.

In some examples, the presence of impingement, e.g., a mechanical collision, may be indicated by the presence of a frequency component in the motion signal during systolic motion of the heartbeat, e.g., the magnitude of the frequency component exceeding or otherwise meeting a threshold. In some examples, impingement may be detected by identifying motion in a direction other than a primary axis of motion during the heartbeat and determining that the motion meets one or more impingement criteria. The primary axis of motion may be a primary axis of systolic motion, and the motion in the direction other than the primary axis meeting the one or more impingement criteria may include an amount or velocity of the motion exceeding (or otherwise meeting) a threshold.

In the event that the impingement is determined to be unacceptable (NO of 306), the clinician may pull tether to recapture PD 12 (308). The clinician may either reposition PD 12 or replace PD 12 with another PD at a location better suited for the implantation. The process may start over by positioning a catheter adjacent a patient tissue at the new location (302). If PD 12 is adequately positioned within the patient (YES of 306), which may include an acceptable level of impingement and satisfaction of other acceptance criteria, e.g., adequate pacing capture threshold and subthreshold impedance, the clinician fully releases IMD 10 from the tether (312). Then, the clinician withdraws the deployment device from the patient, leaving IMD 10 secured within the patient (314).

Although the example method of FIG. 10 illustrates impingement detection as being performed during implantation of PD 12, impingement detection may be performed at any time, such as after PD 12 has been implanted. For example, impingement detection may be performed in response to a command from external device 24, server 142, or computing device 144, or on a periodic basis. The periodic basis may be a beat-to-beat basis, or less frequently, such as according to a X of Y cycle or X cycle every time period schedule, hourly, or daily. For example, impingement detection may be performed for one cardiac cycle out of every ten cycles, or for one cycle every minute.

Further, although described herein in the context of detecting impingement of an IMD with another structure, processing circuitry may evaluate similar features of a motion signal from a motion sensor, such as a three-dimensional accelerometer or gyroscope, to assess proper fixation the IMD, e.g., a PD. For example, if the engagement of one or more fixation elements with patient tissue is incomplete, a PD may move in unexpected ways during the cardiac cycle, e.g., flopping around or twisting—motions that would not normally occur with adequate fixation. The processing circuitry may classify the motion as improper fixation based on a frequency or amount of the motion, e.g., in a direction other than the primary axis of cardiac motion during contraction.

Figure 11:
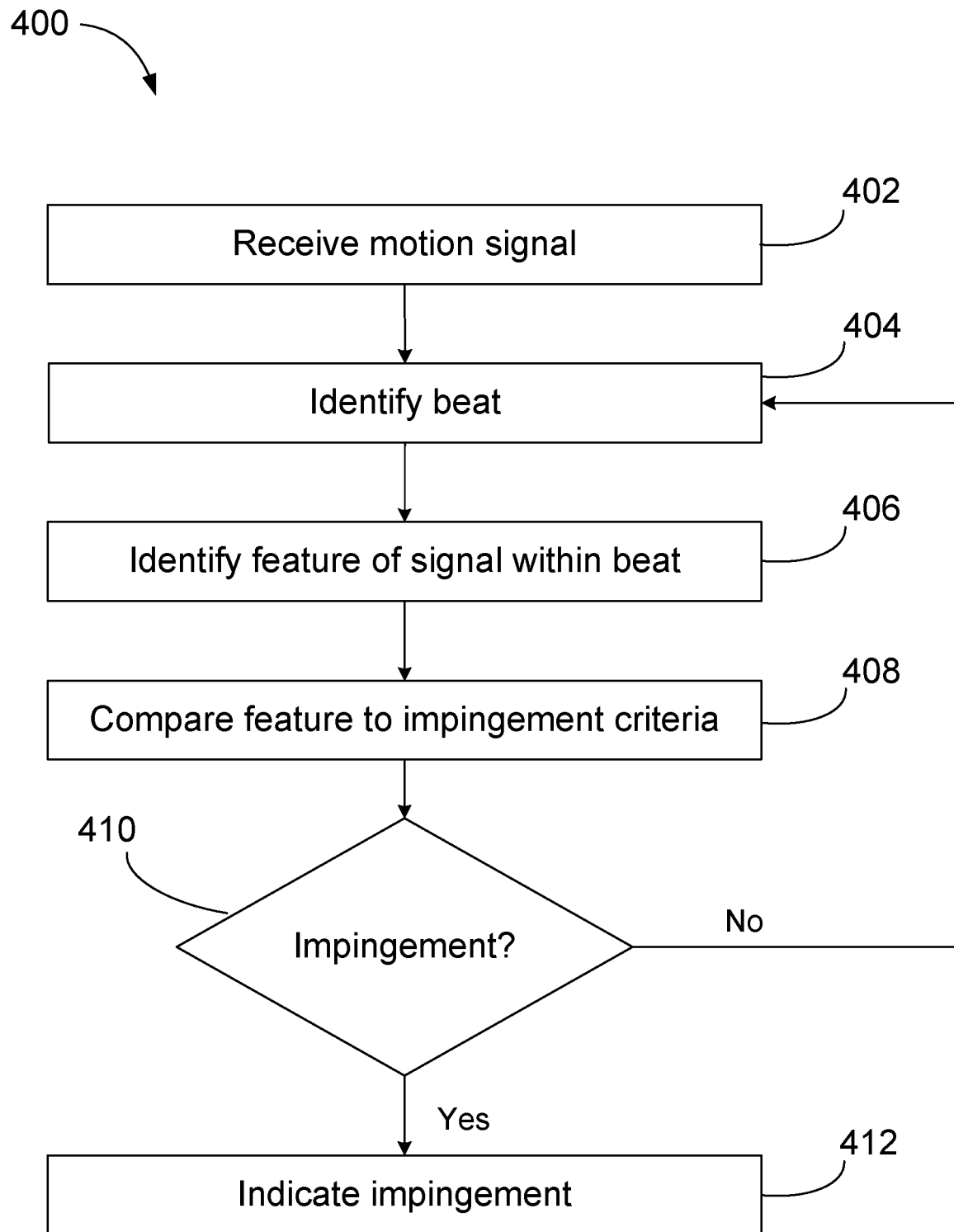
FIG. 11 is a flow diagram illustrating an example process for determining whether impingement is occurring based on an evaluation of the features of a motion signal during a cardiac beat, in accordance with one or more aspects of this disclosure.

FIG. 11 is a flow diagram illustrating an example process for determining whether impingement is occurring based on an evaluation of one or more features of the signal from a motion sensor 100 of PD 12 during a cardiac beat. Although described in the context of an example in which PD 12 and processing circuitry 90 of PD 12 perform a number of the functions illustrated in the example of FIG. 11, in other examples one or more of these functions may be performed by one or more other devices that communicate with PD 12, such as IMD 10, external device 24, external device 142, or computing devices 144, e.g., by the processing circuitry of such devices.

FIG. 11 illustrates an example method for testing whether an impingement should be indicated while using the techniques described herein. The value(s) of the features that indicate whether impingement criteria have been met include, e.g., the magnitude of the motion signal at a certain frequency or within a certain frequency band and the magnitude or amount or velocity of motion in a direction other than the primary axis of motion attributable to the cardiac contraction. The example method of FIG. 11 may be performed during implantation or shortly after implant of PD 12, at a clinic visit, automatically in response to a remote command, and/or on a periodic basis.

According to the example method 400 of FIG. 11, the motion signal is received by processing circuitry 90 of PD 12 from sensor 100, which may be an accelerometer or gyroscope, as examples (402). Again, as discussed herein, the motion signal may be received by processing circuitry of other devices, including but not limited to IMD 10, external device 24, external device 142, and computing devices 144. The processing circuitry at such devices can receive the motion signal. Further, the motion signal may be more than one motion signal, e.g., a signal for each of a two or more axis of a multi-axis accelerometer, in some examples.

Processing circuitry 90 identifies a cardiac beat within the motion signal (404) and identifies features of the signal within the beat (406). Features of the beat used to measure impingement may include, for example, an amount or magnitude of motion, e.g., velocity or displacement, which may be in a direction other than the primary axis, such as in a plane orthogonal to the primary axis of motion during the beat. In some examples, the primary axis of motion comprises a primary axis of systolic motion, and the motion in the direction other than the primary axis meeting the one or more impingement criteria includes an amount of the motion exceeding a threshold. In some examples, the amount of motion is characterized by a sum of the distances, at various points in time during the contraction, from a point of origin of the contraction, or by a maximum distance or another one or more distances from the point of origin.

In addition, features of the beat used to measure impingement may also include, for example, a frequency of the signal during the beat that is atypical for cardiac motion. In some examples, identifying one of the impingements based on the frequency meeting one or more impingement criteria includes a magnitude of frequency component in the signal during systolic motion of the heartbeat exceeding a threshold. Example features of a signal used to measure impingement are illustrated and described in further detail with respect to FIGS. 12A-14.

Processing circuitry 90 compares the identified features of the beat to one or more criteria, which may include comparison to one or more template or threshold values of the feature, as described herein (408). Based on the comparison to one or more templates or threshold values of the feature, processing circuitry 90 may indicate impingement for the beat (410). If impingement is detected (or meets a threshold number or percentage of beats exhibiting impingement (YES of 410), processing circuitry 90 may indicate impingement (412). If impingement is not detected (or does not meet the threshold) (NO of 410), the process may return to the beginning of the method at step 404 and identify the next beat.

As described above, the motion signal, and consequently the features of the beat indicative of impingement, may vary depending on the posture or activity level of the patient. In some examples, processing circuitry 90 may identify the posture or activity level of the patient and adjust one or more aspects of impingement detection to compensate for the posture-based variations. For example, processing circuitry 90 may adjust one or both of the identified features of the signal or the impingement criteria, e.g., according to a function or lookup table, based on the identified posture or activity level.

Although the example techniques of FIGS. 10 and 11 are described primarily in the context of PD 12 implanted in the left-ventricle, other example medical devices may implement the techniques to evaluate the impingement of cardiac structures. In some examples, an extracardiac pacemaker may deliver ventricular pacing through electrodes of one or more leads. The pacemaker may also be coupled to a motion sensor, e.g., by a lead or wirelessly, to receive a motion signal during the heartbeat.

FIGS. 12A and 12B show actual human three-dimensional accelerometer data (in units where 1=the gravitational force of Earth) from a pacing device for a subject with suspected impingement during cardiac contraction. FIG. 12A is a plot illustrating normal sinus rhythm (NSR) emphasizing motion of an IMD, e.g., PD 12, during cardiac contraction, in accordance with one or more aspects of this disclosure. FIG. 12B is a plot illustrating the motion of the IMD with the axes rotated such that the systolic excursion (primary axis) is minimized and the motion orthogonal to the primary axis is emphasized, in accordance with one or more aspects of this disclosure. FIGS. 12A and 12B each show one cardiac cycle. In FIG. 12A, a diastole portion of the cardiac cycle is identified with a solid line and reference item number 510A, a systole portion of the cardiac cycle is identified with a dotted line and reference item number 520A, and a high frequency artifact is identified with a dashed line and reference item number 530A.

In FIG. 12B, the axes have been rotated such that the systolic excursion (primary axis) is minimized. The image thus emphasizes the accelerometer components that are orthogonal to the primary systolic contraction. In FIG. 12B, a diastole portion of the cardiac cycle is identified with a solid line and reference number 510B, a systole portion of the cardiac cycle is identified with a dotted line and reference item number 520B, and a high frequency artifact is identified with a dashed line and reference item number 530B.

Synchronous contraction without impingement may result in predominant acceleration of PD 12 (with physiologic frequency content) in a single direction during systole. By determining an amount or velocity of motion in a direction other than the primary axis of systolic motion, such as in a plane orthogonal to the axis, processing circuitry, e.g., processing circuitry 90 of PD 12, may detect impingement. In some examples, the amount of motion may be a sum of distances from an origin at various points during the systole portion of the cardiac cycle. The amount of motion not associated with the primary movement of the heart during systole may be used, according to the techniques of this disclosure to discriminate beats with impingement.

High frequency content in the acceleration signal may also indicate an impingement, such as a mechanical collision. Processing circuitry 90 may determine the magnitude of the signal at a certain frequency, or within a certain frequency band (such as above a frequency threshold). Processing circuitry 90 may detect impingement during a cardiac beat based on the magnitude meeting a magnitude threshold.

FIGS. 13A and 13B are plots of motion sensor data illustrating motion of the IMD, including the frequency of the motion during systole, in accordance with one or more aspects of this disclosure. FIGS. 13C and 13D are plots of motion sensor data with axes transformed illustrating motion of the IMD in the two axes of the plane that are orthogonal to the primary systolic axis during cardiac contraction, in accordance with one or more aspects of this disclosure. FIGS. 13A and 13C are for Subject 1 who is suspected to have normal motion of the IMD during systole. FIGS. 13B and 13D are for Subject 2 who is suspected to have a collision of the IMD during systole. For FIGS. 13A-D, the plots are for 4 ms samples where 0 is equal to the start of the R-wave, and the subjects 1 and 2 display a narrow intrinsic QRS and have devices implanted in the apex. For FIG. 13A, 610A, 620A, and 630A represent three axes of the same cardiac contraction, and similarly for FIG. 13B, 610B, 620B, and 630B represent three axes of the same cardiac contraction. For FIGS. 13B and 13D, 600B and 600D represent the high frequency artifact.

FIG. 13A shows suspected normal motion of the IMD during systole as having predominantly low frequency and in a single direction. In contrast, FIG. 13B shows the suspected collision motion of the IMD during systole as having a high frequency section 600B, which suggests mechanical collision. In contrast to FIG. 13C, FIG. 13D displays more energy in axes orthogonal to the primary axis of motion during systole, in particular section 600D. The relatively greater amount of orthogonal acceleration may indicate mechanical collision or dyssynchrony.

Figure 14:
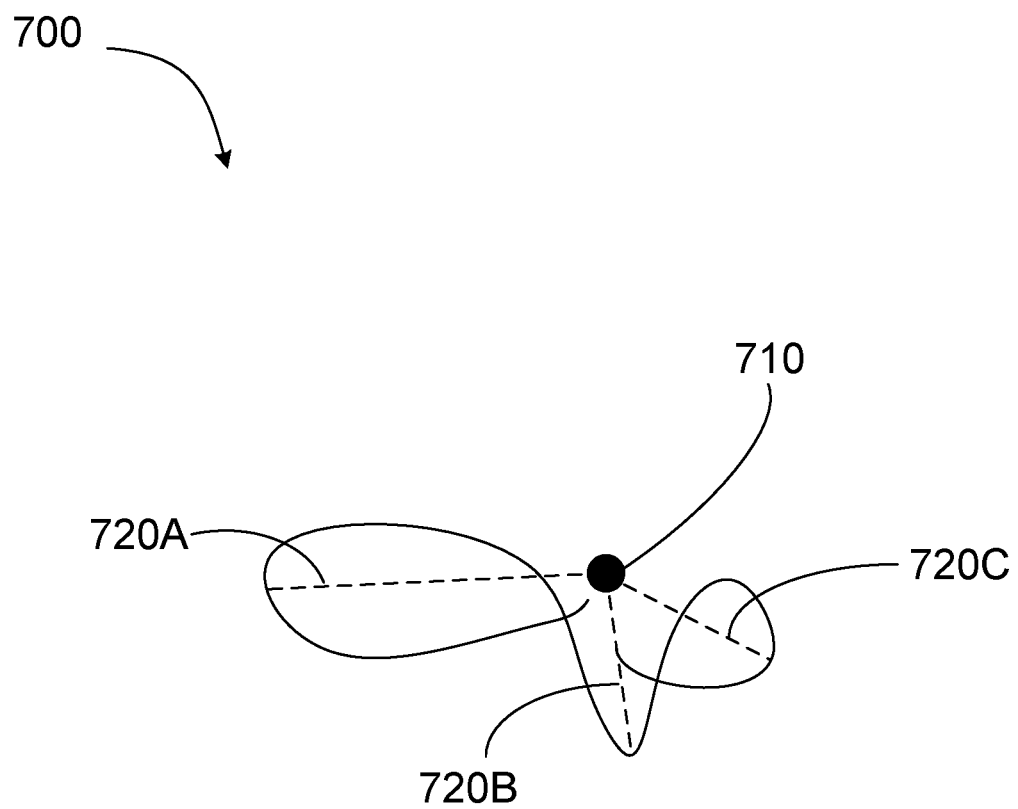
FIG. 14 is a conceptual plot of motion of the IMD during cardiac contraction illustrating example features of the motion signal, in accordance with one or more aspects of this disclosure.

FIG. 14 is a conceptual plot of motion of the IMD during cardiac contraction illustrating example features of the motion signal, in accordance with one or more aspects of this disclosure. FIG. 14 shows a plot illustrating an example of one portion 700 of the signal of a cardiac cycle looking down the primary axis of motion during systole. Vectors 720A, 720B, and 720C (collectively "vectors 720") illustrate motion or displacement from an origin of the contraction 710 in directions other than along the primary axis of motion during systole, e.g., motion in a plane orthogonal to the primary axis, such as due to impingement. Although three vectors 720 are illustrated in FIG. 14, processing circuitry may determine more or fewer vectors 720 to determine impingement as described herein. FIG. 14 shows the beat having a large motion during systole with a vector 720A from origin of the contraction 710. The amount of motion in a direction other than the primary axis of motion, e.g., the maximum, sum, rate of change, or mean of vectors 720, may be used to determine whether impingement has occurred and/or a degree of impingement. Vectors, such as vectors 720B and 720C, with short distances to origin of the contraction 710 may be used to indicate the absence of impingement. While vectors, such as vector 720A, with large distances origin of the contraction 710 may indicate impingement.

The disclosure also contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory. The computer-readable storage media may be referred to as non-transitory. A programmer, such as patient programmer or clinician programmer, or other computing device may also contain a more portable removable memory type to enable easy data transfer or offline data analysis.

In addition, it should be noted that system described herein may not be limited to treatment of a human patient. In alternative examples, the system may be implemented in non-human patients, e.g., primates, canines, equines, pigs, and felines. These other animals may undergo clinical or research therapies that may benefit from the subject matter of this disclosure.

The techniques described in this disclosure, including those attributed to IMD 10, PD 12, external device 24, and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, remote servers, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. For example, any of the techniques or processes described herein may be performed within one device or at least partially distributed amongst two or more devices, such as between IMD 10, PD 12, external device 24. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media.

Various examples have been described. However, other examples are contemplated. For example, although primarily described in the context of a system that includes a single PD and another IMD, e.g., a subcutaneous IMD, used to control CRT pacing by the PD, the techniques described herein may be embodied in any of a variety of systems. As examples, the techniques described herein may be implemented in systems that include one or more PDs, e.g., for bradycardia pacing and/or ATP, systems that do not include another IMD, or systems that include any other implantable or external medical device, such as another, implantable or external pacemaker, cardioverter, defibrillator, neurostimulator, pump, or ventricular assist device. Any such devices may provide off-board processing of a motion signal from an IMD to detect impingement of the IMD. Additionally, although described in the context of the motion signal being additionally used to evaluate contractions for determining whether pace beats achieve fusion, other uses of the motion signal may include determining activity, posture, or sleep of the patient, evaluating cardiac contractions or patient posture or activity to determine whether to deliver an antitachyarrhythmia shock in response to electrogram-based tachyarrhythmia detection, or controlling the speed or other parameters of a ventricular assist device. These and other examples are within the scope of the following claims.

What is claimed is:

1. A system for at least one of delivering cardiac therapy or cardiac sensing, the system comprising:
    an implantable medical device comprising:
        a housing configured for implantation at least one of on or within a heart of a patient;
        at least one fixation element configured to attach the housing to the heart; and
        a sensor configured to produce a signal that indicates motion of the implantable medical device; and
    processing circuitry configured to:
        identify one or more impingements between the housing and another structure based on the signal from the sensor; and
        provide an indication of the one or more impingements to a user.

2. The system of claim 1, wherein the implantable medical device comprises:
    a plurality of electrodes; and
    signal generation circuitry within the housing, the signal generation circuitry configured to deliver cardiac pacing via the plurality of electrodes,
    wherein the processing circuitry comprises processing circuitry of the implantable medical device within the housing configured to control the delivery of pacing by the signal generation circuitry.

3. The system of claim 2, wherein the processing circuitry of the implantable medical device is configured to control the signal generation circuitry to deliver ventricular pacing via the plurality of electrodes.

4. The system of claim 2, wherein the processing circuitry of the implantable medical device is configured to control the signal generation circuitry to deliver cardiac resynchronization therapy via the plurality of electrodes.

5. The system of claim 1, wherein the housing is configured for implantation within the left ventricle of the heart.

6. The system of claim 1, wherein the processing circuitry is configured to identify one or more collisions between the housing and the other structure based on the signal from the sensor.

7. The system of claim 1, wherein the processing circuitry is configured to:
identify a heartbeat; and
identify one of the impingements during the heartbeat.

8. The system of claim 7, wherein the processing circuitry is configured to:
identify a frequency of the signal during the heartbeat; and
identify the one of the impingements based on the frequency meeting one or more impingement criteria.

9. The system of claim 8, wherein the frequency meeting the one or more impingement criteria includes a frequency component in the signal during systolic motion of the heartbeat exceeding a threshold value.

10. The system of claim 7, wherein the processing circuitry is configured to:
identify motion in a direction other than a primary axis of motion during the heartbeat; and
identify the one of the impingements based on the motion in the direction other than the primary axis meeting one or more impingement criteria.

11. The system of claim 10, wherein the primary axis of motion comprises a primary axis of systolic motion, and the motion in the direction other than the primary axis meeting the one or more impingement criteria includes an amount of the motion exceeding a threshold value.

12. The system of claim 1, wherein the sensor comprises a three-dimensional accelerometer.

13. The system of claim 1, wherein the other structure comprises a tissue of the heart.

14. A method for evaluating implantation of an implantable medical device configured for at least one of delivering cardiac therapy or cardiac sensing, wherein the implantable medical device is attached by a fixation element to a heart of a patient, the method comprising:
producing, by a sensor, a signal that is indicative of a motion of the implantable medical device; and
identifying one or more impingements between a housing of the implantable medical device and another structure based on the signal from the sensor.

15. The method of claim 14, wherein the implantable medical device comprises a pacemaker configured to deliver cardiac pacing to the heart.

16. The method of claim 15, wherein the implantable medical device is configured to deliver cardiac resynchronization therapy to at least one ventricle of the heart.

17. The method of claim 14, wherein the implantable medical device is implanted within the heart.

18. The method of claim 14, wherein identifying the one or more impingements comprises identifying, by processing circuitry of the implantable medical device, the one or more impingements based on the signal from the sensor.

19. The method of claim 14, wherein identifying the one or more impingements comprises identifying one or more collisions between the housing and the other structure based on the signal from the sensor.

20. The method of claim 14, wherein identifying the one or more impingements comprises:
identifying a heartbeat; and
identifying one of the impingements during the heartbeat.

21. The method of claim 20, wherein identifying the one or more impingements comprises:
identifying a frequency of the signal during the heartbeat; and
identifying the one of the impingements based on the frequency meeting one or more impingement criteria.

22. The method of claim 21, wherein the frequency meeting the one or more impingement criteria includes a frequency component in the signal during systolic motion of the heartbeat exceeding a threshold value.

23. The method of claim 20, wherein identifying the one or more impingements comprises:
identifying motion in a direction other than a primary axis of motion during the heartbeat; and
identifying the one of the impingements based on the motion in the direction other than the primary axis meeting one or more impingement criteria.

24. The method of claim 23, wherein the primary axis of motion comprises a primary axis of systolic motion, and the motion in the direction other than the primary axis meeting the one or more impingement criteria includes an amount of the motion exceeding a threshold value.

25. The method of claim 14, wherein the sensor comprises a three-dimensional accelerometer.

26. The method of claim 14, wherein identifying the one or more impingements comprises indicating to a user to reposition the implantable medical device.

27. The method of claim 26, wherein repositioning the implantable medical device includes detaching the fixation element from the heart of the patient and attaching the implantable medical device at another location on the heart of the patient.

28. The method of claim 14, wherein identifying the one or more impingements between the housing of the implantable medical device and the other structure comprises identifying one or more impingements between the housing and a cardiac tissue.

29. A system for evaluating implantation of an implantable medical device configured for at least one of delivering cardiac therapy or cardiac sensing, wherein the implantable medical device is attached by a fixation element to a heart of a patient, the system comprising:
means for producing, by a sensor, a signal that is indicative of a motion of the implantable medical device; and
means for identifying one or more impingements between a housing of the implantable medical device and another structure based on the signal from the sensor.

30. A non-transitory computer-readable storage medium comprising instructions that, when executed by processing circuitry of a medical device system for evaluating implantation of an implantable medical device configured for at least one of delivering cardiac therapy or cardiac sensing, wherein the implantable medical device is attached by a fixation element to a heart of a patient, cause the processing circuitry to:
produce, by a sensor, a signal that is indicative of a motion of the implantable medical device; and
identify one or more impingements between a housing of the implantable medical device and another structure based on the signal from the sensor.

31. A system for at least one of delivering cardiac therapy or cardiac sensing, the system comprising:
an implantable medical device comprising:
a housing configured for implantation at least one of on or within a heart of a patient;
at least one fixation element configured to attach the housing to the heart;

a sensor including a three-dimensional accelerometer, the sensor configured to produce a signal that indicates motion of the implantable medical device;
a plurality of electrodes; and
signal generation circuitry within the housing, the signal generation circuitry configured to deliver cardiac pacing via the plurality of electrodes; and
processing circuitry configured to:
  identify a heartbeat;
  identify one or more impingements between the housing and another structure based on the signal from the sensor;
  identify one of the impingements during the heartbeat; and
  provide an indication of the one of the impingements to a user,
wherein the processing circuitry comprises processing circuitry of the implantable medical device within the housing configured to control the delivery of pacing by the signal generation circuitry, and
wherein the housing is configured for implantation within the left ventricle of the heart.

* * * * *